(12) United States Patent
Parkar et al.

(10) Patent No.: US 7,488,799 B2
(45) Date of Patent: Feb. 10, 2009

(54) PROSTAGLANDIN RECEPTOR PROTEIN

(75) Inventors: Ashfaq Parkar, Princeton, NJ (US); Paul August, Boxford, MA (US); Theresa Kuntzweiler, Bernardsville, NJ (US); Mohamad Ali Ardati, Basking Ridge, NJ (US); Namadev Baskaran, Acton, MA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 23 days.

(21) Appl. No.: 11/621,164

(22) Filed: Jan. 9, 2007

(65) Prior Publication Data

US 2008/0020403 A1 Jan. 24, 2008

Related U.S. Application Data

(62) Division of application No. 10/747,994, filed on Dec. 30, 2003, now Pat. No. 7,183,062.

(51) Int. Cl.
*C07K 1/00* (2006.01)
*C07K 14/00* (2006.01)
*C07K 17/00* (2006.01)
*C07K 16/00* (2006.01)
*C08H 1/00* (2006.01)

(52) U.S. Cl. ..................... 530/350; 530/402
(58) Field of Classification Search .............. None
See application file for complete search history.

(56) References Cited

U.S. PATENT DOCUMENTS 5,958,723 A 9/1999 Abramovitz et al.
6,214,972 B1 4/2001 Abramovitz et al.
6,395,499 B1 5/2002 Abramovitz et al.

FOREIGN PATENT DOCUMENTS

WO WO 96/23066 8/1996

OTHER PUBLICATIONS

Arimura Akinori et al., Prevention Of Allergic Inflammation By A Novel Protaglandin Receptor Antagonist, S-5751, The Journal Of Pharmacology And Experimental Therapeutics, (2001), vol. 298, No. 2, pp. 411-419.
Armstrong Roma A., Platelet Prostanoid Receptors, Pharmacol. Ther., (1996), vol. 72, No. 3, pp. 171-191.
Brightling C. E. et al., New Insights Into The Role Of The Mast Cell In Asthma, Clin. Exp. Allergy, (2003), vol. 33, pp. 550-556.
Coleman Robert A. et al., International Union Of Pharmacology Classification Of Prostanoid Receptor: Properties, Distribution, And Structure Of The Receptors And Their Subtypes, Pharmacological Reviews, (1994), vol. 46, No. 2, pp. 205-229.
Doyle William J. et al., Physiologic Responses To Intranasal Dose-Response Challenges With Histamine, Methacholine, Bradykinin, And Prostaglandin In Adult Volunteers With And Without Nasal Allergy, Journal Of Allergy And Clinical Immunology, (1990), vol. 86, pp. 924-935.
Hirata Masakazu et al., Molecular Characterization Of A Mouse Prostaglanding D Receptor And Functional Expression Of The Cloned Gene, Proc. Nat'l. Acad. Sci. USA, (1994), vol. 91, pp. 11192-11196.
Holgate Stephen T. et al., Bronchial Epithelium As A Key Regulator Of Airway Allergen Sensitization And Remodeling Is Asthma, Am. J. Respir. Crit. Care Med., (2000), vol. 162, pp. S113-S117.
Kobayashi Takuya et al., Amino Acid Residues Conferring Ligand Binding Properties Of Prostaglandin I And Prostaglandin D Receptors, The Journal Of Biological Chemistry, (2000), vol. 276, No. 32, pp. 24294-24303.
Lewis Robert A. et al., Prostaglandin D2 Generation After Activation Of Rat And Human Mast Cells With Anti-IgE, The Journal Of Immunology, (1982), vol. 129, No. 4, pp. 1627-1631.
Matsuoka Toshiyuki et al., Prostaglandin D2 As A Mediator Of Allergic Asthma, Science, (2000), vol. 287, pp. 2013-2019.
Narumiya Shuh et al., Structure And Function Of Prostanoid Receptors, Journal Of Lipid Mediators, (1993), vol. 6, pp. 155-161.
Negishi Manabu et al., Prostanoid Receptors And Their Biological Actions, Prog. Lipid Res., (1993), vol. 32, No. 4, pp. 417-434.
Roberts L. Jackson et al., Increased Production Of Prostaglandin D2 In Patients With Systemic Mastocytosis, The New England Journal Of Medicine, (1980), vol. 303, No. 24, pp. 1400-1404.
Wright D. Hamish et al., A Novel Biological Role For Prostaglandin D2 Is Suggested By Distribution Studies Of The Rat DP Prostanoid Receptor, European Journal Of Pharmacology, (1999), vol. 377, pp. 101-115.

*Primary Examiner*—Robert Landsman
(74) *Attorney, Agent, or Firm*—Ann Marie Szczepanik

(57) ABSTRACT

Described herein is a novel member of the prostanoid receptor family, a guinea pig prostaglandin D2 receptor. Described are the receptor, the nucleic acid that encodes it, and various uses for both.

5 Claims, 7 Drawing Sheets

ATGTCCTTCTATCCCTGCAACACCACCGCCTCGGTACGGAGTGGGAACTC
GGCGACGGTGGGCGGGGAGTGCTCTTCAGCGCGGGCCTCCTGGGCAACCTGC
TGGCCCTAGCGCTGCTGGCACGCTCGGGCTCGGGCTCCTGCCGGCCGGC
CCGCAGCCCTCAGTCTCTACGTGCTGGTGTGCGGCTTGACGGTCACAGA
CCTGCTAGGCAAGTGCCTGGTGAGCCCGGTGTGCTGCTGCCTATGCGC
AAAACCGGAGCCTCAGGGACTGGCACCCGGCAGGGCGACTCGCTGTGC
CAAGCCTTCGCCTTCATCATCGTCCTTCTTTGGGCTCGCCTCGACGCTCCA
GCTCTTAGCCATGGCCCTAGAGTGCTGGCTGTCCCTGGGACACCCTTCT
TCTACCAGCGGCACATCACTGTGCGCCGGGCGTGCTCGTGGCGCCGGCT
GTGGGCGCCTTCAGCCTGGCTTCTGCGCCTCCCCCTCGTGGGCTTCGG
GAACTTGTGCAGTACTGTCCCGGCACCTGGTGTTTCTTCCAGATGATCT
CCGGGACGACTCGCCGTCGGTGAAGGGCTACTCGGTGCTGTACTCCACC
CTCATGGCCGTGTTGGTGCTCGCCATCGTGCTGCAACCTGGGCGCCAT
GCGCAAACCTCTACACCATGCACCAGCGCCTGCGACGGCACACGCGCTGCT
GCAGCCTCCGGGACCGGCGGGCGGGAGGCGTTTCCGCAATCCTTGGAGGAG
CTGGACCACCACTGTGCTGCTGCCCTCATGACCCGTGCTCTTCACCATGTG
CACTCTGCCGTTAGTTATCGCGGCTTACTATGGAGCATTAAAGCTGTCG
AAGAGGAGCCCGACGACCTCCTAGCCTTGCGTTTTCTCTCTGATTTCA
ATCGTGGACCCTTGGATCTTTATCATAAGAACCTCTTCTTACCGAAACTGCACT
GTTTTTCACAAGATTTTCATAAGACCTCTCTTTTACGAAACTGCACT
GCCACTTCTACCAAACTAAGCGTGGAATCCAGTCTGTGA

Figure 1

MSFYPCNTTASVRSGNSATVGGVLFSAGLLGNLLALALLARSGLGSCRPRPQPSVFYVLVCGLT
VTDLLGKCLVSPVVLAAYAQNRSLRGLAPAQGDSLCQAFAFIMSFFGLASTLQLLAMALECWL
SLGHPFFYQRHITVRRGVLVAPAVGAFSLAFCALPFVGFGNFVQYCPGTWCFFQMISGDDSPSV
KGYSVLYSTLMALLVLAIVLCNLGAMRNLYTMHQRLRRHTRCCSLRDRAGEAFPQSLEELDHL
LLLALMTVLFTMCTLPLVYRAYYGAFKAVEEEPDDLLALRFLSVISIVDPWIFIIFRTSVFRMFFH
KIFIRPLLYRNWHCHFYQTNVESSL

Figure 2

SEQUENCE LISTING

<160> NUMBER OF SEQ ID NOS: 18

<210> SEQ ID NO 1
<211> LENGTH: 1038
<212> TYPE: DNA
<213> ORGANISM: Cavia porcellus

```
<400> SEQUENCE: 1
atgtccttct atccctgcaa caccaccgcc tcggtacgga gtgggaactc ggcgacggtg      60
ggcggagtgc tcttcagcgc gggcctcctg ggcaacctgc tggccctagc gctgctggca     120 cgctcgggc tcgggtcctg ccggccgcgc ccgcagccct cagtcttcta cgtgctggtg      180
tgcggcttga cggtcacaga cctgctaggc aagtgcctgg tgagcccggt ggtgctggct     240
gcctatgcgc aaaaccggag cctcagggga ctggcacccg cgcagggcga ctcgctgtgc     300
caagccttcg ccttcatcat gtccttcttt gggctcgcct cgacgctcca gctcttagcc     360
atggccctag agtgctggct gtccctggga caccccttct tctaccagcg gcacatcact     420
gtgcgccggg gcgtgctcgt ggcgccggct gtgggcgcct tcagcctggc tttctgcgcg     480
ctccccttcg tgggcttcgg gaactttgtg cagtactgtc ccggcacctg tgtttcttc      540 cagatgatct ccggggacga ctcgccgtcg gtgaagggct actcggtgct gtactccacc     600
ctcatggcgc tgttggtgct cgccatcgtg ctgtgcaacc tgggcgccat gcgcaacctc     660
tacaccatgc accagcgcct gcgacggcac acgcgctgct gcagcctccg ggaccgcgcg     720
ggcgaggcgt ttccgcaatc cttggaggag ctggaccacc tgctgctgct ggccctcatg     780
accgtgctct tcaccatgtg cactctgccg ttagtttatc gcgcttacta tggagcattt     840
aaagctgtcg aagaggagcc cgacgacctc ctagccttgc gttttctctc tgtgatttca     900
atcgtggacc cttggatctt tatcattttc agaacttcag tatttcggat gttttttcac     960
aagattttca taagacctct tctttaccga aactggcact gccacttcta ccaaactaac    1020
gtggaatcca gtctgtga                                                  1038

<210> SEQ ID NO 2
<211> LENGTH: 345
<212> TYPE: PRT
<213> ORGANISM: Cavia porcellus

<400> SEQUENCE: 2

Met Ser Phe Tyr Pro Cys Asn Thr Thr Ala Ser Val Arg Ser Gly Asn
 1               5                  10                  15

Ser Ala Thr Val Gly Gly Val Leu Phe Ser Ala Gly Leu Leu Gly Asn
                20                  25                  30

Leu Leu Ala Leu Ala Leu Leu Ala Arg Ser Gly Leu Gly Ser Cys Arg
            35                  40                  45

Pro Arg Pro Gln Pro Ser Val Phe Tyr Val Leu Val Cys Gly Leu Thr
        50                  55                  60

Val Thr Asp Leu Leu Gly Lys Cys Leu Val Ser Pro Val Val Leu Ala
 65                  70                  75                  80

Ala Tyr Ala Gln Asn Arg Ser Leu Arg Gly Leu Ala Pro Ala Gln Gly
                85                  90                  95

Asp Ser Leu Cys Gln Ala Phe Ala Phe Ile Met Ser Phe Phe Gly Leu
            100                 105                 110

Ala Ser Thr Leu Gln Leu Leu Ala Met Ala Leu Glu Cys Trp Leu Ser
        115                 120                 125

Leu Gly His Pro Phe Phe Tyr Gln Arg His Ile Thr Val Arg Arg Gly
    130                 135                 140

Val Leu Val Ala Pro Ala Val Gly Ala Phe Ser Leu Ala Phe Cys Ala
145                 150                 155                 160

Leu Pro Phe Val Gly Phe Gly Asn Phe Val Gln Tyr Cys Pro Gly Thr
                165                 170                 175
```

-continued

```
Trp Cys Phe Phe Gln Met Ile Ser Gly Asp Asp Ser Pro Ser Val Lys
            180                 185                 190

Gly Tyr Ser Val Leu Tyr Ser Thr Leu Met Ala Leu Leu Val Leu Ala
        195                 200                 205

Ile Val Leu Cys Asn Leu Gly Ala Met Arg Asn Leu Tyr Thr Met His
    210                 215                 220

Gln Arg Leu Arg Arg His Thr Arg Cys Cys Ser Leu Arg Asp Arg Ala
225                 230                 235                 240

Gly Glu Ala Phe Pro Gln Ser Leu Glu Glu Leu Asp His Leu Leu Leu
                245                 250                 255

Leu Ala Leu Met Thr Val Leu Phe Thr Met Cys Thr Leu Pro Leu Val
            260                 265                 270

Tyr Arg Ala Tyr Tyr Gly Ala Phe Lys Ala Val Glu Glu Glu Pro Asp
        275                 280                 285

Asp Leu Leu Ala Leu Arg Phe Leu Ser Val Ile Ser Ile Val Asp Pro
    290                 295                 300

Trp Ile Phe Ile Ile Phe Arg Thr Ser Val Phe Arg Met Phe Phe His
305                 310                 315                 320

Lys Ile Phe Ile Arg Pro Leu Leu Tyr Arg Asn Trp His Cys His Phe
                325                 330                 335

Tyr Gln Thr Asn Val Glu Ser Ser Leu
            340                 345

<210> SEQ ID NO 3
<211> LENGTH: 21
<212> TYPE: DNA
<213> ORGANISM: Artificial
<220> FEATURE:
<223> OTHER INFORMATION: 675_Topo_F3 primer

<400> SEQUENCE: 3
gggacaccct tcttctaca a                                      21

<210> SEQ ID NO 4
<211> LENGTH: 22
<212> TYPE: DNA
<213> ORGANISM: Artificial
<220> FEATURE:
<223> OTHER INFORMATION: 675_Topo_R2 primer

<400> SEQUENCE: 4
gaacacatgg tgaagagcac tg                                    22

<210> SEQ ID NO 5
<211> LENGTH: 20
<212> TYPE: DNA
<213> ORGANISM: Artificial
<220> FEATURE:
<223> OTHER INFORMATION: 675_GP_3'RACE_F primer

<400> SEQUENCE: 5
gtgctcgtgg cgccggtgtg                                       20

<210> SEQ ID NO 6
<211> LENGTH: 25
<212> TYPE: DNA
<213> ORGANISM: Artificial
<220> FEATURE:
<223> OTHER INFORMATION: 675_Rev_P2 primer

<400> SEQUENCE: 6
```

```
<210> SEQ ID NO 7
<211> LENGTH: 28
<212> TYPE: DNA
<213> ORGANISM: Artificial
<220> FEATURE:
<223> OTHER INFORMATION: 675_RACE_R9 primer

<400> SEQUENCE: 7
tcaccaggca cttgcctagc aggtctgt                                    28

<210> SEQ ID NO 8
<211> LENGTH: 39
<212> TYPE: DNA
<213> ORGANISM: Artificial
<220> FEATURE:
<223> OTHER INFORMATION: GW675 forward primer

<400> SEQUENCE: 8
aaaagcaggc ttaggaatgt ccttctatcc ctgcaacac                        39

<210> SEQ ID NO 9
<211> LENGTH: 37
<212> TYPE: DNA
<213> ORGANISM: Artificial
<220> FEATURE:
<223> OTHER INFORMATION: GW675 reverse primer

<400> SEQUENCE: 9
aagaaagctg ggtctcacag actggattcc acgttag                          37

<210> SEQ ID NO 10
<211> LENGTH: 9
<212> TYPE: PRT
<213> ORGANISM: Cavia porcellus

<400> SEQUENCE: 10

Gln Tyr Cys Pro Gly Thr Trp Cys Arg
1               5

<210> SEQ ID NO 11
<211> LENGTH: 15
<212> TYPE: PRT
<213> ORGANISM: Cavia porcellus

<400> SEQUENCE: 11

Arg Phe Leu Ser Val Ile Ser Ile Val Asp Pro Trp Ile Phe Ile
1               5                   10                  15

<210> SEQ ID NO 12
<211> LENGTH: 1080
<212> TYPE: DNA
<213> ORGANISM: Homo sapiens

<400> SEQUENCE: 12
atgaagtcgc cgttctaccg ctgccagaac accacctctg tggaaaaagg caactcggcg    60
gtgatgggcg gggtgctctt cagcaccggc ctcctgggca acctgctggc cctggggctg   120
ctggcgcgct cggggctggg gtggtgctcg cggcgtccac tgcgcccgct gccctcggtc   180
ttctacatgc tggtgtgtgg cctgacggtc accgacttgc tgggcaagtg cctcctaagc   240
ccggtggtgc tggctgccta cgctcagaac cggagtctgc gggtgcttgc gcccgcattg   300
gacaactcgt tgtgccaagc cttcgccttc ttcatgtcct tctttgggct ctcctcgaca   360
```

| | |
|---|---|
| ctgcaactcc tggccatggc actggagtgc tggctctccc tagggcaccc tttcttctac | 420 |
| cgacggcaca tcaccctgcg cctgggcgca ctggtggccc cggtggtgag cgccttctcc | 480 |
| ctggctttct gcgcgctacc tttcatgggc ttcgggaagt tcgtgcagta ctgccccggc | 540 |
| acctggtgct ttatccagat ggtccacgag agggctcgc tgtcggtgct ggggtactct | 600 |
| gtgctctact ccagcctcat ggcgctgctg gtcctcgcca ccgtgctgtg caacctcggc | 660 |
| gccatgcgca acctctatgc gatgcaccgg cggctgcagc ggcacccgcg ctcctgcacc | 720 |
| agggactgtg ccgagccgcg cgcggacggg agggaagcgt ccctcagcc cctggaggag | 780 |
| ctggatcacc tcctgctgct ggcgctgatg accgtgctct cactatgtg ttctctgccc | 840 |
| gtaatttatc gcgcttacta tggagcattt aaggatgtca aggagaaaaa caggacctct | 900 |
| gaagaagcag aagacctccg agccttgcga tttctatctg tgatttcaat tgtggaccct | 960 |
| tggattttta tcattttcag atctccagta tttcggatat ttttcacaa gattttcatt | 1020 |
| agacctctta ggtacaggag ccggtgcagc aattccacta acatggaatc cagtctgtga | 1080 |

<210> SEQ ID NO 13
<211> LENGTH: 1074
<212> TYPE: DNA
<213> ORGANISM: Rattus norvegicus

<400> SEQUENCE: 13

| | |
|---|---|
| atgaatgagt cctatcgctg tcaggcagcc acctgggtgg aacggggctc ctcagcgaca | 60 |
| atgggtggtg tgctcttcag tgcaggactg ctgggcaatc tcctggcgct ggtgctgctg | 120 |
| gcgcgatccg ggctggggtc ctgccggcca gggccactgc atccgccgcc ctcggtcttt | 180 |
| tatgtgctag tgtgcggctt gacggtcacc cacttgctgg gcaagtgtct gatcagcccg | 240 |
| atggtcctgg ctgcctacgc gcaaaatcgg agcctaaagg aactgctgcc tgcctcaggc | 300 |
| aatcagttat gtgaagcctt cgccttcctg atgtccttct ttgggttagc ctcgaccttg | 360 |
| cagctactgg ctatggcact ggagtgctgg ctgtctctgg acaccctttt cttctaccaa | 420 |
| aggcacatca ccgcccgccg gggagtgctg gtggcgccag tcgcaggcgc cttctctttg | 480 |
| gctttctgtg cgctccccttt gctggctttt gggaagttcg tgcagtactg tccaggtacc | 540 |
| tggtgcttca tccagatgat ccacaagaag cgctcattct cggtaatagg cttctctgtg | 600 |
| ctctactcca gcctcatggc gctgctggtc ctcgcaactg tggtgtgcaa cctgggtgcc | 660 |
| atgtccaacc tctatgccat gcacaggcgc cagaggcacc atccccgccg ctgctccagg | 720 |
| gaccgcgccc agtcaggctc agactacagg catgggtccc cgaatccttt ggaggagctg | 780 |
| gaccactttg ttctgctggc tctcacgaca gtgctcttca ccatgtgttc cctgcctta | 840 |
| atttatcgtg cttactatgg agcctttaaa cttgtggaca gagctgacgg agactcggaa | 900 |
| gacctccaag ccttgcgttt tctgtctgtg atttccatcg tggaccctg gatcttcatc | 960 |
| atttcagga cttcagtatt ccggatgtta tttcacaagg ctttcacaag acctctgatc | 1020 |
| tacagaaact ggtgcagcca ttcctggcag actaacatgg aatccacttt gtga | 1074 |

<210> SEQ ID NO 14
<211> LENGTH: 1074
<212> TYPE: DNA
<213> ORGANISM: Mus musculus

<400> SEQUENCE: 14

| | |
|---|---|
| atgaacgagt cctatcgctg tcagacatcc acctgggtgg aaagggggctc ctcggcgacg | 60 |

-continued

```
atgggcgctg tgctcttcgg tgcggggctt ctgggcaatc ttctggcgct ggtgctgctg     120
gcgcgctcgg gactggggtc ttgccggcca gggccactac acccgccgcc ctcggtcttt     180
tatgtgctcg tgtgtggctt gacggtcacc gacttgctgg caattgtctc gatcagcccg     240
atggtcctgg ctgcctacgc gcaaaaccag agcctaaagg aactgctgcc tgcctcaggc     300
aatcagttat gcgaaacgtt cgccttcctg atgtccttct ttgggctagc ctcgacctta     360
cagctgttgg ctatggcggt ggagtgctgg ctgtctctgg acacccctt cttctaccaa      420
aggcacgtca ccttgcgccg gggagtgctg gtggcaccgg tcgtggccgc cttctgcttg     480
gctttctgtg cgctccccctt tgctggtttt gggaagttcg tgcagtactg tccaggcacc    540
tggtgtttca tccagatgat ccacaaggag cgttcatttt cggtaatagg cttctctgtg     600
ctctactcca gcctcatggc gctgctggtc tcgcaaccg tggtgtgcaa cctgggtgcc      660
atgtacaacc tctatgacat gcacaggcgc cagaggcact atcctcaccg ctgctccagg     720
gaccgcgccc agtcaggctc agactacagg cacgggtccc tgcatccttt ggaggagctg     780
gaccactttg tgctgctggc tctcatgaca gtgctcttca ccatgtgttc cctgccttta     840
atttatcgtg cgtactatgg agcctttaaa cttgagaaca aagctgaagg agactcagaa     900
gacctccaag ccttgcgttt cctgtctgtg atttccatag tggaccctg gatcttcatc      960
atcttcagga cttcagtatt ccggatgtta tttcacaagg ttttcacaag acctctgatc    1020
tacagaaact ggagcagcca ttcccagcaa agtaacgtgg aatccacttt gtga          1074
```

<210> SEQ ID NO 15
<211> LENGTH: 359
<212> TYPE: PRT
<213> ORGANISM: Homo sapiens

<400> SEQUENCE: 15

```
Met Lys Ser Pro Phe Tyr Arg Cys Gln Asn Thr Thr Ser Val Glu Lys
  1               5                  10                  15

Gly Asn Ser Ala Val Met Gly Gly Val Leu Phe Ser Thr Gly Leu Leu
             20                  25                  30

Gly Asn Leu Leu Ala Leu Gly Leu Leu Ala Arg Ser Gly Leu Gly Trp
         35                  40                  45

Cys Ser Arg Arg Pro Leu Arg Pro Leu Pro Ser Val Phe Tyr Met Leu
     50                  55                  60

Val Cys Gly Leu Thr Val Thr Asp Leu Leu Gly Lys Cys Leu Leu Ser
 65                  70                  75                  80

Pro Val Val Leu Ala Ala Tyr Ala Gln Asn Arg Ser Leu Arg Val Leu
                 85                  90                  95

Ala Pro Ala Leu Asp Asn Ser Leu Cys Gln Ala Phe Ala Phe Phe Met
            100                 105                 110

Ser Phe Phe Gly Leu Ser Ser Thr Leu Gln Leu Leu Ala Met Ala Leu
        115                 120                 125

Glu Cys Trp Leu Ser Leu Gly His Pro Phe Phe Tyr Arg Arg His Ile
    130                 135                 140

Thr Leu Arg Leu Gly Ala Leu Val Ala Pro Val Ser Ala Phe Ser
145                 150                 155                 160

Leu Ala Phe Cys Ala Leu Pro Phe Met Gly Phe Gly Lys Phe Val Gln
                165                 170                 175

Tyr Cys Pro Gly Thr Trp Cys Phe Ile Gln Met Val His Glu Glu Gly
            180                 185                 190

Ser Leu Ser Val Leu Gly Tyr Ser Val Leu Tyr Ser Ser Leu Met Ala
```

```
                195                 200                 205
Leu Leu Val Leu Ala Thr Val Leu Cys Asn Leu Gly Ala Met Arg Asn
    210                 215                 220

Leu Tyr Ala Met His Arg Arg Leu Gln Arg His Pro Arg Ser Cys Thr
225                 230                 235                 240

Arg Asp Cys Ala Glu Pro Arg Ala Asp Gly Arg Glu Ala Ser Pro Gln
            245                 250                 255

Pro Leu Glu Glu Leu Asp His Leu Leu Leu Ala Leu Met Thr Val
            260                 265                 270

Leu Phe Thr Met Cys Ser Leu Pro Val Ile Tyr Arg Ala Tyr Tyr Gly
        275                 280                 285

Ala Phe Lys Asp Val Lys Glu Lys Asn Arg Thr Ser Glu Glu Ala Glu
    290                 295                 300

Asp Leu Arg Ala Leu Arg Phe Leu Ser Val Ile Ser Ile Val Asp Pro
305                 310                 315                 320

Trp Ile Phe Ile Ile Phe Arg Ser Pro Val Phe Arg Ile Phe Phe His
                325                 330                 335

Lys Ile Phe Ile Arg Pro Leu Arg Tyr Arg Ser Arg Cys Ser Asn Ser
            340                 345                 350

Thr Asn Met Glu Ser Ser Leu
        355

<210> SEQ ID NO 16
<211> LENGTH: 357
<212> TYPE: PRT
<213> ORGANISM: Rattus norvegicus

<400> SEQUENCE: 16

Met Asn Glu Ser Tyr Arg Cys Gln Ala Ala Thr Trp Val Glu Arg Gly
1               5                   10                  15

Ser Ser Ala Thr Met Gly Gly Val Ala Phe Ser Ala Gly Leu Leu Gly
            20                  25                  30

Asn Leu Leu Ala Leu Val Leu Leu Ala Arg Ser Gly Leu Gly Ser Cys
        35                  40                  45

Arg Pro Gly Pro Leu His Pro Pro Ser Val Phe Tyr Val Leu Val
    50                  55                  60

Cys Gly Leu Thr Val Thr Asp Leu Leu Gly Lys Cys Leu Ile Ser Pro
65                  70                  75                  80

Met Val Leu Ala Ala Tyr Ala Gln Asn Arg Ser Leu Lys Glu Leu Leu
                85                  90                  95

Pro Ala Ser Gly Asn Gln Leu Cys Glu Ala Phe Ala Phe Leu Met Ser
            100                 105                 110

Phe Phe Gly Leu Ala Ser Thr Leu Gln Leu Leu Ala Met Ala Leu Glu
        115                 120                 125

Cys Trp Leu Ser Leu Gly His Pro Phe Phe Tyr Gln Arg His Ile Thr
    130                 135                 140

Ala Arg Arg Gly Val Leu Val Ala Pro Val Ala Gly Ala Phe Ser Leu
145                 150                 155                 160

Ala Phe Cys Ala Leu Pro Phe Ala Gly Phe Gly Lys Phe Val Gln Tyr
                165                 170                 175

Cys Pro Gly Thr Trp Cys Phe Ile Gln Met Ile His Lys Lys Arg Ser
            180                 185                 190

Phe Ser Val Ile Gly Phe Ser Val Leu Tyr Ser Ser Leu Met Ala Leu
        195                 200                 205
```

```
Leu Val Leu Ala Thr Val Val Cys Asn Leu Gly Ala Met Ser Asn Leu
    210                 215                 220

Tyr Ala Met His Arg Arg Gln Arg His His Pro Arg Arg Cys Ser Arg
225                 230                 235                 240

Asp Arg Ala Gln Ser Gly Ser Asp Tyr Arg His Gly Ser Pro Asn Pro
                245                 250                 255

Leu Glu Glu Leu Asp His Phe Val Leu Ala Leu Thr Thr Val Leu
        260                 265                 270

Phe Thr Met Cys Ser Leu Pro Leu Ile Tyr Arg Ala Tyr Tyr Gly Ala
            275                 280                 285

Phe Lys Leu Val Asp Arg Ala Asp Gly Asp Ser Glu Asp Leu Gln Ala
    290                 295                 300

Leu Arg Phe Leu Ser Val Ile Ser Ile Val Asp Pro Trp Ile Phe Ile
305                 310                 315                 320

Ile Phe Arg Thr Ser Val Phe Arg Met Leu Phe His Lys Thr Phe Thr
                325                 330                 335

Arg Pro Leu Ile Tyr Arg Asn Trp Cys Ser His Ser Trp Gln Thr Asn
                340                 345                 350

Met Glu Ser Thr Leu
        355

<210> SEQ ID NO 17
<211> LENGTH: 357
<212> TYPE: PRT
<213> ORGANISM: Mus musculus

<400> SEQUENCE: 17

Met Asn Glu Ser Tyr Arg Cys Gln Thr Ser Thr Trp Val Glu Arg Gly
1               5                   10                  15

Ser Ser Ala Thr Met Gly Ala Val Leu Phe Gly Ala Gly Leu Leu Gly
            20                  25                  30

Asn Leu Leu Ala Leu Val Leu Leu Ala Arg Ser Gly Leu Gly Ser Cys
        35                  40                  45

Arg Pro Gly Pro Leu His Pro Pro Ser Val Phe Tyr Val Leu Val
50                  55                  60

Cys Gly Leu Thr Val Thr Asp Leu Leu Gly Lys Cys Leu Ile Ser Pro
65                  70                  75                  80

Met Val Leu Ala Ala Tyr Ala Gln Asn Gln Ser Leu Lys Glu Leu Leu
                85                  90                  95

Pro Ala Ser Gly Asn Gln Leu Cys Glu Thr Phe Ala Phe Leu Met Ser
                100                 105                 110

Phe Phe Gly Leu Ala Ser Thr Leu Gln Leu Leu Ala Met Ala Val Glu
            115                 120                 125

Cys Trp Leu Ser Leu Gly His Pro Phe Phe Tyr Gln Arg His Val Thr
    130                 135                 140

Leu Arg Arg Gly Val Leu Val Ala Pro Val Val Ala Ala Phe Cys Leu
145                 150                 155                 160

Ala Phe Cys Ala Leu Pro Phe Ala Gly Phe Gly Lys Phe Val Gln Tyr
                165                 170                 175

Cys Pro Gly Thr Trp Cys Phe Ile Gln Met Ile His Lys Glu Arg Ser
            180                 185                 190

Phe Ser Val Ile Gly Phe Ser Val Leu Tyr Ser Ser Leu Met Ala Leu
        195                 200                 205

Leu Val Leu Ala Thr Val Val Cys Asn Leu Gly Ala Met Tyr Asn Leu
    210                 215                 220
```

```
Tyr Asp Met His Arg Arg Gln Arg His Tyr Pro His Arg Cys Ser Arg
225                 230                 235                 240

Asp Arg Ala Gln Ser Gly Ser Asp Tyr Arg His Gly Ser Leu His Pro
            245                 250                 255

Leu Glu Glu Leu Asp His Phe Val Leu Leu Ala Leu Met Thr Val Leu
        260                 265                 270

Phe Thr Met Cys Ser Leu Pro Leu Ile Tyr Arg Ala Tyr Tyr Gly Ala
        275                 280                 285

Phe Lys Leu Glu Asn Lys Ala Glu Gly Asp Ser Glu Asp Leu Gln Ala
        290                 295                 300

Leu Arg Phe Leu Ser Val Ile Ser Ile Val Asp Pro Trp Ile Phe Ile
305                 310                 315                 320

Ile Phe Arg Thr Ser Val Phe Arg Met Leu Phe His Lys Val Phe Thr
                325                 330                 335

Arg Pro Leu Ile Tyr Arg Asn Trp Ser Ser His Ser Gln Gln Ser Asn
                340                 345                 350

Val Glu Ser Thr Leu
            355

<210> SEQ ID NO 18
<211> LENGTH: 359
<212> TYPE: PRT
<213> ORGANISM: Artificial
<220> FEATURE:
<223> OTHER INFORMATION: majority sequence of guinea pig, human, mouse
      and rat
<220> FEATURE:
<221> NAME/KEY: MISC_FEATURE
<222> LOCATION: (294)..(294)
<223> OTHER INFORMATION: E, K, N or D
<220> FEATURE:
<221> NAME/KEY: MISC_FEATURE
<222> LOCATION: (298)..(298)
<223> OTHER INFORMATION: S, E or D
<220> FEATURE:
<221> NAME/KEY: MISC_FEATURE
<222> LOCATION: (347)..(347)
<223> OTHER INFORMATION: C or S
<220> FEATURE:
<221> NAME/KEY: MISC_FEATURE
<222> LOCATION: (351)..(351)
<223> OTHER INFORMATION: Y, N, Q or W

<400> SEQUENCE: 18

Met Asn Glu Ser Phe Tyr Arg Cys Gln Thr Thr Thr Ser Val Glu Arg
1               5                   10                  15

Gly Ser Ser Ala Thr Met Gly Gly Val Leu Phe Ser Ala Gly Leu Leu
            20                  25                  30

Gly Asn Leu Leu Ala Leu Val Leu Leu Ala Arg Ser Gly Leu Gly Ser
        35                  40                  45

Cys Arg Pro Gly Pro Leu His Pro Pro Ser Val Phe Tyr Val Leu
    50                  55                  60

Val Cys Gly Leu Thr Val Thr Asp Leu Leu Gly Lys Cys Leu Ile Ser
65                  70                  75                  80

Pro Val Val Leu Ala Ala Tyr Ala Gln Asn Arg Ser Leu Lys Glu Leu
                85                  90                  95

Ala Pro Ala Ser Gly Asn Ser Leu Cys Glu Ala Phe Ala Phe Leu Met
            100                 105                 110

Ser Phe Phe Gly Leu Ala Ser Thr Leu Gln Leu Leu Ala Met Ala Leu
        115                 120                 125
```

-continued

```
Glu Cys Trp Leu Ser Leu Gly His Pro Phe Phe Tyr Gln Arg His Ile
    130                 135                 140
Thr Leu Arg Arg Gly Val Leu Val Ala Pro Val Val Gly Ala Phe Ser
145                 150                 155                 160
Leu Ala Phe Cys Ala Leu Pro Phe Ala Gly Phe Gly Lys Phe Val Gln
                165                 170                 175
Tyr Cys Pro Gly Thr Trp Cys Phe Ile Gln Met Ile His Lys Glu Arg
            180                 185                 190
Ser Phe Ser Val Ile Gly Phe Ser Val Leu Tyr Ser Ser Leu Met Ala
        195                 200                 205
Leu Leu Val Leu Ala Thr Val Val Cys Asn Leu Gly Ala Met Arg Asn
210                 215                 220
Leu Tyr Ala Met His Arg Arg Leu Arg His His Pro Arg Arg Cys Ser
225                 230                 235                 240
Arg Asp Arg Ala Gln Ser Gly Ser Asp Tyr Arg Glu Gly Ser Pro Gln
                245                 250                 255
Pro Leu Glu Glu Leu Asp His Leu Val Leu Leu Ala Leu Met Thr Val
            260                 265                 270
Leu Phe Thr Met Cys Ser Leu Pro Leu Ile Tyr Arg Ala Tyr Tyr Gly
        275                 280                 285
Ala Phe Lys Leu Val Xaa Glu Arg Ala Xaa Gly Asp Ser Glu Asp Leu
290                 295                 300
Gln Ala Leu Arg Phe Leu Ser Val Ile Ser Ile Val Asp Pro Trp Ile
305                 310                 315                 320
Phe Ile Ile Phe Arg Thr Ser Val Phe Arg Met Leu Phe His Lys Ile
                325                 330                 335
Phe Ile Arg Pro Leu Ile Tyr Arg Asn Trp Xaa Ser His Ser Xaa Gln
            340                 345                 350
Thr Asn Val Glu Ser Ser Leu
                355
```

PROSTAGLANDIN RECEPTOR PROTEIN

CROSS REFERENCE TO RELATED APPLICATIONS

This application is a divisional application of U.S. application Ser. No. 10/747,994 filed on Dec. 30, 2003, now U.S. Pat. No. 7,183,062 issued Feb. 27, 2007, the disclosure of which is incorporated herein in its entirety.

FIELD OF THE INVENTION

The present invention relates generally to a nucleic acid molecule that encodes a heretofore unknown member of the prostanoid receptor family.

BACKGROUND OF THE INVENTION

Prostanoids, including prostaglandin (PG), prostacyclin and thromboxane (TX), are important mediators of central and peripheral physiological effects. Prostaglandin D2 (PGD2) is formed in a variety of tissues including brain, spleen, lung, bone marrow, stomach, skin and also in mast cells (Lewis et al., 1982). PGD2 has been implicated in many physiological events both in the central nervous system and in the peripheral tissues. In the central nervous system, PGD2 has been shown to affect the induction of sleep, body temperature, olfactory function, hormone release and nociception. Peripherally, PGD2 is the major cyclooxygenase product of arachidonic acid produced from mast cells following immunological challenge. Local allergen challenge in patients with allergic rhinitis, bronchial asthma, allergic conjunctivitis and atopic dermatitis has been shown to result in rapid elevation of PGD2 levels in nasal and bronchial lavage fluids, tears and skin chamber fluids. Activated mast cells, a major source of PGD2, are one of the key players in driving the allergic response in conditions such as asthma, allergic rhinitis, allergic conjunctivitis, allergic dermatitis and other diseases (Brightling et al., 2003). Likewise, PGD2 has many inflammatory actions, such as increasing vascular permeability in the conjunctiva and skin, increasing nasal airway resistance, airway narrowing and eosinophil infiltration into the conjunctiva and trachea. Therefore, PGD2 is considered one of the key players in driving inflammatory reactions.

Early efforts have focused on identifying distinct receptors for the five naturally occurring bioactive prostanoids, $PGD_2$, $PGE_2$, $PGF_{2\alpha}$, $PGI_2$ and $TXA_2$, resulting in the classification of five basic types of prostanoid receptors: DP, EP, FP, prostacyclin (IP) and thomboxane (TP) receptors, respectively (Coleman et al., 1994). Many of the actions of prostaglandin D2 are mediated through its action on the D-type prostaglandin receptor (DP), a G protein-coupled receptor. While originally thought that each prostanoid acted preferentially on individual receptors, researchers studying prostanoid biology have begun to appreciate the promiscuity of these ligands to interact with members of the different receptor families. Thus, it is becoming ever more clear that to understand prostanoid signaling one must elucidate the biological consequence of prostanoid receptor activation.

The DP receptor is of particular interest because it is found in both central and peripheral cells suggesting its involvement in mediating varied biological pathways and, consequently, its potential therapeutic importance in many disease states. DP receptors have been identified in the brain and $PGD_2$ has effects on sleep induction, body temperature, olfactory function, and hormone release (Negishi, et al., 1993; Wright et al., 1999 and references within). DP receptors have also been localized to discrete and distinct cell populations of the spinal cord. This observation may explain the discordant effects of hyperalgesia and allodynia (discomfort from innocuous tactile stimuli) induced by $PGD_2$. DP receptors are also present in the gastrointestinal tract and have been implicated in the contractile response of the GI tract (Wright et al., 1999; Ito et al., 1989). Additionally, DP receptor ligands have been shown to induce mucous secretion and cell proliferation of intestinal cells. Glycogenesis in the liver may also be regulated by DP receptors (Ito et al., 1989). DP receptors are found in the eye and agonists reduce intraoccular pressure suggesting a role in glaucoma. Platelets contain the DP receptor and $PGD_2$ has been shown to inhibit platelet aggregation supporting a role for the DP receptor in modulating blood disorders such as thrombosis (Armstrong, 1996). Thus, the varied expression of the DP receptor in different organs and tissues suggests the DP receptor may be an attractive target for different therapeutic areas.

Of particular interest, the DP receptor has been implicated in various inflammatory disorders including but not limited to asthma, allergic rhinitis, airway hyperactivity, allergic dermatitis, allergic conjunctivitis and chronic obstructive pulmonary disease. This is supported by the observation that $PGD_2$ is the major prostanoid released by immunochallenged mast cells (Roberts, et al., 1980). In asthma, the respiratory epithelium has long been recognized as a key source of inflammatory cytokines and chemokines that drive the progression of the disease (Holgate et al., 2000). In an experimental murine model of asthma, the DP receptor is dramatically upregulated on airway epithelium on antigen challenge (Matsuoka et al., 2000). Conversely, in knockout mice lacking the DP receptor, there is a marked reduction in airway hyperreactivity and chronic inflammation (Matsuoka et al., 2000); two of the cardinal features of human asthma. Similarly, DP receptor antagonists have been shown to reduce airway inflammation in a guinea pig experimental asthma model (Arimura et al., 2001). The DP receptor is also thought to be involved in human allergic rhinitis, a frequent allergic disease that is characterized by the symptoms of sneezing, itching, rhinorea and nasal congestion. Local administration of $PGD_2$ to the nose causes a dose dependent increase in nasal congestion (Doyle et al. 1990). DP antagonists have been shown to be effective at alleviating the symptoms of allergic rhinitis in multiple species, and more specifically, have been shown to inhibit the antigen-induced nasal congestion, the most manifest symptom of allergic rhinitis. DP antagonists are also effective in experimental models of allergic conjunctivitis and allergic dermatitis (Arimura et al., 2001). Thus, DP antagonists could therefore be useful in the treatment of a variety of PGD2-mediated disorders including, but not limited to, bronchial asthma, Chronic obstructive pulmonary disease (COPD), allergic rhinitis, allergic dermatitis, allergic conjunctivitis, systemic mastocytosis and ischemic repurfusion injury.

Thus far, the DP receptor has been cloned from human (Boie et al., 1995), rat (Wright et al., 1999) and mouse (Hirata et al., 1994). These DP receptors share 73-90% homology at the amino acid level between human, mouse and rat and, in each case, activation of the recombinant receptors leads to accumulation of intracellular cAMP. It is generally observed between G protein coupled receptors that compounds often show varying potencies from one orthologue receptor to another.

Disclosed here, for the first time, is a DP receptor from the guinea pig. The present invention provides several advantages over that which is currently known in the art. Species differences between mouse, rat, human and guinea pig can now be more fully determined and characterized. The low expression levels of the DP receptor in native tissues makes it difficult to assess a compound's activity as a modulator, effector, agonist or antagonist of the receptor. The present invention now provides the opportunity to examine the receptor in an isolated and purified condition providing the ability to test compounds and then to bridge in vitro studies to the same species in vivo. Because of its larger size, the guinea pig is a preferred animal model to smaller rodents, for instance, providing more surface area with regard to dermatology and gastrointestinal studies. More importantly, the guinea pig is the most usable small animal model for some allergy models such as nasal congestion and is more responsive to airway hyperactivity manipulations. Although the guinea pig represents an ideal preclinical model for the evaluation of DP receptor modulators in multiple disease models, as outlined above, the cloning of the guinea DP receptor has not previously been reported and hence it is difficult to predict the affinity of a compound against this orthologue.

BRIEF DESCRIPTION OF THE DRAWINGS

FIG. 1 shows a nucleic acid sequence of the receptor of the invention (SEQ ID NO:1).

FIG. 2 shows an amino acid sequence of the receptor of the invention (SEQ ID NO:2).

DETAILED DESCRIPTION OF THE INVENTION

Figure 3:
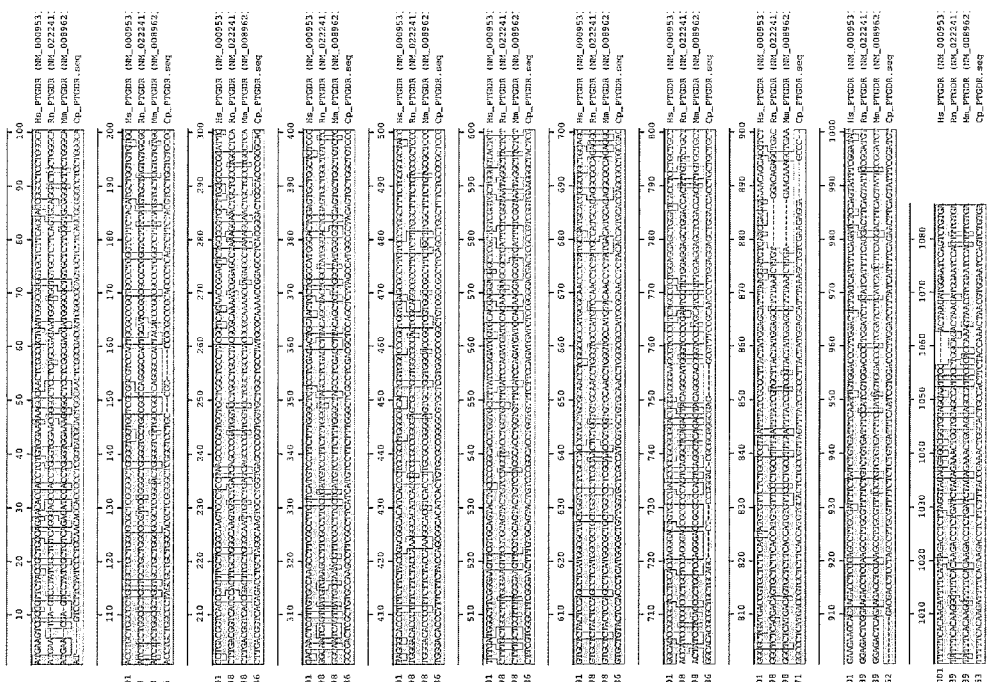
FIG. 3 shows an alignment of the coding sequences of the DP receptor between multiple species. Shaded residues match the guinea pig residues exactly. Hs=human (SEQ ID NO: 12); Rn=rat (SEQ ID NO: 13); Mm=mouse (SEQ ID NO: 14); and Cp=guinea pig (SEQ ID NO: 1).
Figure 4:
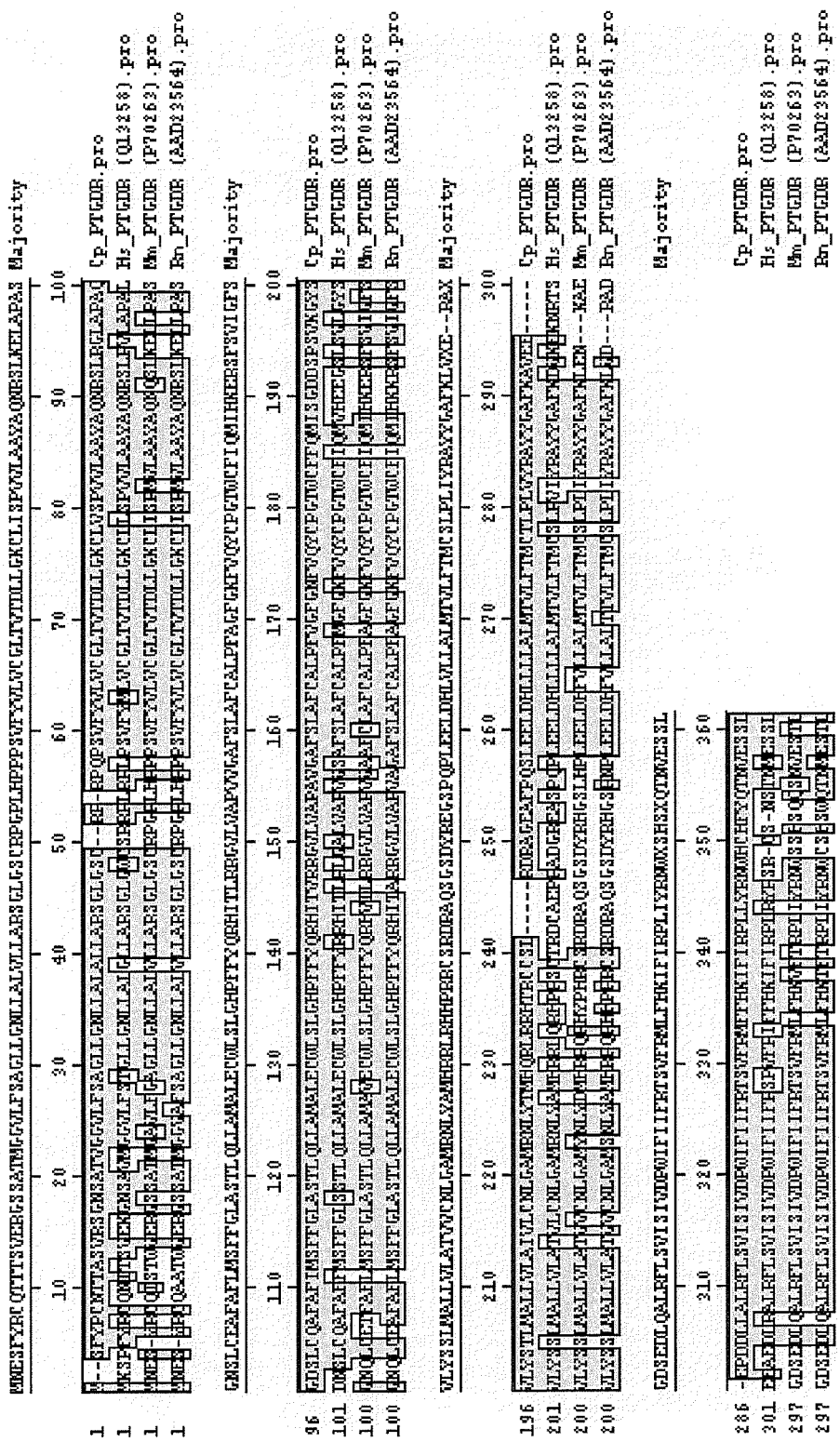
FIG. 4 shows an alignment of the amino acid sequences of the DP receptor between multiple species. Shaded residues match the guinea pig residues exactly. Hs=human (SEQ ID NO: 15); Rn=rat (SEQ ID NO: 16); Mm=mouse (SEQ ID NO: 17); Cp=guinea pig (SEQ ID NO: 2); Majority (SEQ ID NO: 18).

The present invention relates to isolated nucleic acid and protein forms that represent but are not necessarily limited to the prostanoid receptor family. In a preferred embodiment, the isolated nucleic acid and protein represents the guinea pig DP receptor. Various aspects of the invention are described in further detail in the following subsections.

Definitions

As used herein, "nucleic acid molecule" refers to the phosphate ester polymeric form of ribonucleosides (adenosine, guanosine, uridine or cytidine; "RNA") or deoxyribonucleosides (deoxyadenosine, deoxyguanosine, deoxythymidine, or deoxycytidine; "DNA") or any phosphorester analogs thereof, such as phosphorothioates and thioesters, in either single stranded form, or double stranded helix form. The nucleic acid molecule may include a deoxyribonucleic acid molecule (DNA), such as genomic DNA and complementary DNA (cDNA) that may be coding or noncoding single-stranded or double stranded, synthetic DNA, ribonucleic acid (RNA) molecule that may be single-stranded or double-stranded and analogs of the DNA and RNA generated using nucleotide analogs. Double stranded DNA:DNA, DNA:RNA and RNA:RNA helices are possible.

As used herein, an "isolated" or "purified" nucleic acid molecule is one that is separated from other nucleic acid molecules that are present in the natural source of the nucleic acid. Preferably, the "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. In various embodiments, the isolated nucleic acid molecule can contain less than about 5 kb, 4 kb, 3 kb, 2 kb, 1 kb, 0.5 kb or 0.1 kb of nucleotide sequences that flank the nucleotide molecule of the present invention. For example, these flanking nucleotide sequences may be sequences that naturally flank the nucleotide molecule in genomic DNA of the cell from which the nucleic acid was isolated. A nucleic acid may be considered isolated when it has been substantially removed from its endogenous environment to enable manipulation by one skilled in the art, such as but not limited to nucleotide sequencing, restriction digestion, site-directed mutagenesis, and subcloning into expression vectors. The nucleic acid may be present in whole cells or cell lysates or in partially purified or substantially purified form. A nucleic acid purified from cells is substantially free of other cellular material or culture medium. A chemically synthesized nucleic acid is purified when it is substantially free of chemical precursors or other chemicals.

The term "recombinant," when used in connection with a polypeptide, refers to a polypeptide derived from the translation of a recombinant polynucleotide, that is, a polynucleotide that is isolated or purified (as defined above) or that is otherwise not in its native state. The term includes, for example, those polypeptides that are expressed by or contained within cells that contain either a cloning vector or expression vector, as well as synthetic polypeptides.

As used herein, the term "modulator" refers to a moiety (e.g., but not limited to, a ligand and a candidate compound) that modulates the activity of the receptor protein of the present invention. A modulator of the present invention may be an agonist, a partial agonist, an antagonist, or an inverse agonist.

As used herein, the term "agonist" refers to moieties (e.g., but not limited to, ligands and candidate compounds) that activate the intracellular response when bound to the receptor, or enhance GTP binding to membranes.

As used herein, the term "partial agonist" refers to moieties (e.g., but not limited to, ligands and candidate compounds) that activate the intracellular response when bound to the receptor to a lesser degree/extent than do agonists, or enhance GTP binding to membranes to a lesser degree/extent than do agonists.

As used herein, the term "antagonist" refers to moieties (e.g., but not limited to, ligands and candidate compounds) that competitively bind to the receptor at the same site as does an agonist. However, an antagonist does not activate the intracellular response initiated by the active form of the receptor and thereby can inhibit the intracellular responses by agonists or partial agonists. In a related aspect, antagonists do not diminish the baseline intracellular response in the absence of an agonist or partial agonist.

As used herein, the term "inverse agonist" refers to moieties (e.g., but not limited to, ligand and candidate compound) that bind to a constitutively active receptor and inhibit the baseline intracellular response. The baseline response is initiated by the active form of the receptor below the normal base level of activity that is observed in the absence of agonists or partial agonists, or decrease of GTP binding to membranes.

As used herein, the term "candidate compound" refers to a moiety (e.g., but not limited to, a chemical compound) that is amenable to a screening technique. In one embodiment, the term does not include compounds that were publicly known to be compounds selected from the group consisting of agonist, partial agonist, inverse agonist or antagonist. Those compounds were identified by traditional drug discovery processes involving identification of an endogenous ligand specific for a receptor, and/or screening of candidate compounds against a receptor wherein such a screening requires a competitive assay to assess efficacy.

As used herein, the terms "constitutively activated receptor" or "autonomously active receptor," are used herein interchangeably, and refer to a receptor subject to activation in the absence of ligand. Such constitutively active receptors can be endogenous or non-endogenous (i.e., GPCRs can be modified by recombinant means to produce mutant constitutive forms of wild-type GPCRs; e.g., see EP 1071701; WO 00/22129; WO 00/22131; and U.S. Pat. Nos. 6,150,393 and 6,140,509 which are hereby incorporated by reference in their entireties).

As used herein, the term "constitutive receptor activation" refers to the stabilization of a receptor in the active state by means other than binding of the receptor with the endogenous ligand or chemical equivalent thereof.

As used herein, the term "ligand" refers to a moiety that binds to another molecule, wherein the moiety includes, but certainly is not limited to a hormone or a neurotransmitter, and further, wherein the moiety stereoselectively binds to a receptor.

As used herein, the term "family," when referring to a protein or a nucleic acid molecule of the invention, is intended to mean two or more proteins or nucleic acid molecules having a seemingly common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that second protein. Members of a family also may have common functional characteristics.

As used herein interchangeably, the terms "activity", "biological activity" and "functional activity", refer to an activity exerted by a protein, polypeptide or nucleic acid molecule of the present invention on a responsive cell as determined in vivo or in vitro, according to standard techniques. An activity can be a direct activity, such as an association with or an enzymatic activity on a second protein or an indirect activity, such as a cellular signaling activity mediated by interaction of the protein of the present invention with a second protein. In a particular embodiment, an activity includes, but is not limited to at least one or more of the following activities: (i) the ability to interact with proteins in the signaling pathway; (ii) the ability to interact with a ligand; and (iii) the ability to interact with an intracellular target protein.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture [R. I. Freshney, ed. (1986)]*; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "vector" is a replicon, such as plasmid, phage or cosmid, to name only a few, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. Particular examples of vectors are described infra.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

"Homologous recombination" refers to the insertion of a foreign DNA sequence of a vector in a chromosome. In particular, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Isolated Nucleic Acid Molecules

An aspect of the invention relates to isolated or purified nucleic acid molecules that encode the receptor proteins of the invention or portions thereof. The nucleic acid molecule of the present invention or a complement of the nucleic acid sequence can be isolated using standard molecular biology techniques and the sequence information provided in the present invention. Using all or a portion of the nucleic acid sequence of SEQ NO:1 as a hybridization probe, nucleic acid molecules of the invention can be isolated using standard hybridization and cloning techniques (Sambrook et al., 1989). Oligonucleotides corresponding to SEQ ID NO:1, or a portion thereof, can be prepared by standard synthetic techniques, e.g., using an automated DNA synthesizer. The nucleic acid molecule of the invention, or part thereof, can be amplified using cDNA, mRNA or genomic DNA as a template and appropriate oligonucleotide primers according to standard PCR amplification techniques.

The nucleic acid molecule of the invention can comprise a portion of SEQ ID NO:1. The nucleic acid fragment can be used as a probe or primer or the fragment can encode a protein fragment that may or may not be a biologically active portion of the receptor such as the ligand binding domain. For instance, the arginine in the seventh transmembrane domain was proposed to be the binding site for the carboxyl group of the prostanoid molecule (Narumiya et al., 1993) and Lys-75 and Leu-83 of the second transmembrane domain in the mouse confers ligand binding specificity (Kobayashi et al., 2000). These two sequence stretches have previously been reported to be characteristically conserved amongst GPCRs of the prostanoid family (Hirata et al., 1994) and are also present in the guinea pig DP protein: QYCPGTWCR (SEQ ID NO: 10) in the second extracellular loop and RFLSVI-SIVDPWIFI (SEQ ID NO: 11) in the seventh transmembrane domain were identical among all DP orthologues. The nucleotide sequence of SEQ ID NO:1 allows for the generation of probes and primers for the use of identifying and/or cloning the receptor of the invention or homologues in cells, tissues and organs. The oligonucleotide typically comprises a region of nucleotide sequence that hybridizes under stringent conditions to at least 10, preferably about 12, more preferably 25, 50, 75, 100, 125, 150, 175, 200, 250, 300, 350 or 400 consecutive nucleotides of the sense or antisense sequence of SEQ ID NO:1 or of a naturally occurring or man-made mutation of SEQ ID NO:1. The probe may comprise a label group attached thereto, e.g., a radioisotope, a fluorescent compound, an enzyme or an enzyme co-factor. The probe can be part of a kit for identifying cells or tissues encoding the nucleic acid, detecting mRNA levels or determining whether a genomic gene has been mutated or deleted.

The present invention further extends to an isolated nucleic acid molecule that is 90% homologous to SEQ ID NO:1. Sequences that are substantially homologous can be identified by comparing the sequences using standard software available in sequence data banks using default parameters, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

DNA sequence polymorphisms may exist within a population due to natural allelic variation. An allele is one group of genes that occur alternatively at a given genetic locus. As used herein, the terms "gene" and "recombinant gene" refer to nucleic acid molecules comprising an open reading frame encoding the receptor protein of the invention, preferably a guinea pig receptor protein. As used herein, the phrase "allelic variant" refers to a nucleotide sequence that occurs at the gene locus or to a polypeptide encoded by the nucleotide sequence. Alternative alleles can be identified by sequencing the gene of interest in a number of different individuals. Any and all such nucleotide variations and resulting amino acid polymorphisms or variations that are the result of natural allelic variation and that do not alter the functional activity of the receptor of the invention are intended to be within the scope of the invention.

A nucleic acid fragment encoding a "biologically active" or "biologically relevant" portion can be prepared by isolating a portion of SEQ ID NO:1 that encodes a polypeptide having the biological activity of the receptor of the invention. For instance, expressing the encoded portion of the receptor protein (e.g., by recombinant expression in vitro) of the ligand-binding domain or the signal-transducing domain and then assessing the activity of that encoded portion of the receptor. The invention further encompasses nucleic acid molecules that differ from the nucleotide sequence of SEQ ID NO:1 due to degeneracy of the genetic code and thus encode same protein as that encoded by the nucleotide sequence of SEQ ID NO:1. For example, the inventors have identified two potential N-glycosylation sites, Asn-7 in the amino terminus and Asn-86 in the first extracellular loop. Additionally, there are also two potential protein kinase C phosphorylation sites, Ser-46 and Thr-140 located in the first and third cytoplasmic loops, respectively.

In addition to naturally occurring allelic variants, it is known by those skilled in the art that there is substantial amount of redundancy in the various codons that code for specific amino acids. Thus, the invention is directed to those DNA sequences encoding RNA comprising alternative codons or RNA sequences encoding alternative codons which code for the eventual translation of the identical amino acid sequence of SEQ ID NO:2 or portions thereof. It is well known in the art that the following codons can be used interchangeably to code for each specific amino acid:

| Amino Acid | Codons |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |

|                              | -continued                          |
|------------------------------|-------------------------------------|
| Glutamine (Gln or Q)         | CAA or CAG                          |
| Asparagine (Asn or N)        | AAU or AAC                          |
| Lysine (Lys or K)            | AAA or AAG                          |
| Aspartic Acid (Asp or D)     | GAU or GAC                          |
| Glutamic Acid (Glu or E)     | GAA or GAG                          |
| Cysteine (Cys or C)          | UGU or UGC                          |
| Arginine (Arg or R)          | CGU or CGC or CGA or CGG or AGA or AGG |
| Glycine (Gly or G)           | GGU or GGC or GGA or GGG            |
| Tryptophan (Trp or W)        | UGG                                 |
| Termination codon            | UAA or UAG or UGA                   |

It should be understood that the codons specified above are for RNA sequences. The corresponding codons for DNA have a T substituted for U.

A person skilled in the art can further appreciate that changes can be introduced into SEQ ID NO:1 by mutation without altering the biological activity of the encoded protein. A "non-essential" amino acid residue is a residue that can be altered from the wild-type sequence, e.g., the sequence of SEQ ID NO:2 without altering the biological activity whereas the "essential" amino acid residues are required for biological activity. Thus, amino acid residues that are not conserved or only semi-conserved among several species may be non-essential and likely targets for alteration. Another aspect of the invention pertains to nucleic acid molecules encoding proteins of the invention that contain changes in amino acid residues that are not essential for activity. Such proteins differ in amino acid sequence from SEQ ID NO:1 yet retain biological activity. An isolated nucleic acid molecule encoding a protein having a sequence that differs from that of SEQ ID NO:2 can be created by introducing one or more nucleotide substitutions, additions or deletions into the nucleotide sequence of SEQ ID NO:1.

Mutations can be introduced by standard techniques such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue with a similar side chain. Families of amino acid residues having similar side chains have been defined in the art. For example, families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The sequence analysis of the guinea pig receptor provided below in "Example 3" that compares the sequence of the guinea pig to human, rat and mouse provides guidance in the selection of non-essential amino acids. Thus, a predicted nonessential amino acid residue would preferably be replaced with another amino acid residue from the same side chain family. Alternatively, mutations can be introduced randomly along the coding region or portions thereof, such as by saturation mutagenesis, and the resulting mutants screened for biological activity to identify mutants that retain activity. Following mutagenesis, the encoded protein can be expressed recombinantly and the activity of the protein determined. In a preferred embodiment, the mutant protein can be assayed for the ability to form protein:protein interactions such as with proteins in the prostanoid signaling pathway; the ability to bind ligands such as ligands that bind to the prostanoid receptor; or, the ability to bind to intracellular target proteins. The present invention also relates to native or mutant proteins or protein fragments of diagnostic, therapeutic or prophylactic use and would be useful for screening for agonists, antagonists or modulators of receptor function.

Nucleotide sequences coding for a peptide may be altered so as to code for a protein having properties that are different than those of the naturally occurring peptide, such as changing the affinity of the ligand binding domain or modulating the signal transduction pathway. The present invention also relates to alterations of the nucleic acid sequence of SEQ ID NO:1 or portions thereof that modify the biological activity of the protein.

Hybridization of Isolated Nucleic Acid Molecules

A nucleic acid molecule is "hybridizable" to another nucleic acid molecule, such as a cDNA, genomic DNA, or RNA, when a single stranded form of the nucleic acid molecule can anneal to another nucleic acid molecule under the appropriate conditions of temperature and solution ionic strength (see Sambrook et al., supra). The conditions of temperature and ionic strength determine the "stringency" of the hybridization. Low stringency hybridization conditions correspond to a $T_m$ of 55° C. (e.g., 5× sodium chloride/sodium citrate (SSC), 0.1% SDS, 0.25% milk, and no formamide; or 30% formamide, 5×SSC, 0.5% SDS). Moderate stringency hybridization conditions correspond to a higher $T_m$, (e.g., 40% formamide, with 5× or 6×SSC). High stringency hybridization conditions correspond to the highest $T_m$, (e.g., 50% formamide, 5× or 6×SSC). Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid molecule is at least about 20 nucleotides; particularly at least about 30 nucleotides; more particularly at least about 40 nucleotides, even more particularly about 50 nucleotides, and yet more particularly at least about 60 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

In a particular embodiment of the present invention, a hybridizable nucleic acid molecule of the invention is at least 300, 325, 350, 375, 400, 425, 450, 500, 550, 600, 650, 700, 800, 900 or 1000 nucleotides in length and hybridizes under stringent conditions to the nucleic acid molecule comprising the nucleotide sequence, preferably the coding sequence, of SEQ ID NO:1 a complement thereof, or a fragment thereof. The term "hybridizes under stringent conditions" is intended to describe conditions for hybridization and washing under which nucleotide sequences at least 55%, 60%, 65%, 70% and preferably 75% or more complementary to each other typically remain hybridized. Such stringent conditions are known to those skilled in the art and can be found in "Current Protocols in Molecular Biology", John Wiley & Sons, N.Y. (1989), 6.3.1-6.3.6. A preferred, non-limiting example of stringent hybridization conditions are hybridization in 6×SSC at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1 or the complement thereof corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). One skilled in the art will appreciate that the conditions may be modified in view of sequence-specific variables (e.g., length, G-C richness etc.). In another embodiment, an isolated nucleic acid molecule of the invention that hybridizes under stringent conditions to a potion of the sequence of SEQ ID NO:1 can be used as a probe or a primer. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1 or of a naturally occurring mutant of SEQ ID NO:1.

Antisense Nucleic Acid Molecules

The present invention encompasses antisense nucleic acid molecules, i.e., molecules that are complementary to a sense nucleic acid encoding a protein (e.g., complementary to the coding strand of a double-stranded cDNA molecule or complementary to an mRNA sequence). An antisense nucleic acid can hydrogen bond to a sense nucleic acid. The antisense nucleic acid can be complementary to an entire nucleic acid sequence of SEQ ID NO:1 or a portion thereof. Given the coding strand sequences disclosed herein (e.g., SEQ ID NO:1), antisense nucleic acids of the invention can be designed according to the rules of Watson & Crick base pairing. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be synthesized chemically using naturally occurring nucleotides or various chemically modified nucleotides designed to increase the biological stability of the molecules, or to increase the physical stability of the duplex formed between the antisense and sense nucleic acids, e.g., phosphorothioate derivatives, phosphonate derivatives and acridine-substituted nucleotides can be used.

Examples of modified nucleotides that can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, β-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, β-D-mannosylqueosine, 5-methoxycarboxymethyluracil, 5-methoxyuracil, 2-methylthio-$N^6$-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil and 2,6-diaminopurine. Alternatively, the antisense nucleic acid can be produced biologically by using an expression vector into which the nucleic acid has been subcloned in an antisense orientation (i.e., RNA transcribed from the inserted nucleic acid will be of an antisense orientation to a target nucleic acid of interest).

The antisense nucleic acid molecules of the invention typically are administered to a subject or generated in situ so as to hybridize with or bind to cellular mRNA and/or genomic DNA encoding the protein of the invention, thereby inhibiting expression of the protein by inhibiting transcription and/or translation. The hybridization can be by conventional nucleotide complementarity to form a stable duplex, or, for example, in the case of an antisense nucleic acid molecules that bind to DNA duplexes, through specific interactions in the major groove of the double helix, or to a regulatory region.

An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that the molecules specifically bind to receptors or antigens expressed on a selected cell surface, e.g., by linking the antisense nucleic acid molecules to peptides or antibodies that bind to cell surface receptors or antigens. The antisense nucleic acid molecules also can be delivered to cells using the vectors described herein. To achieve sufficient intracelluar concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in that the strands run parallel to each other (Gaultier et al., Nucleic Acids Res (1987)15:6625-6641). The antisense nucleic acid molecule also can comprise a methylribonucleotide (Inoue et al., Nucleic Acids Res (1987) 15:6131-6148) or a chimeric RNA-DNA analogue (Inoue et al., FEBS Lett (1987) 215:327-330).

Ribozymes

The invention also encompasses ribozymes. Ribozymes are catalytic RNA molecules with ribonuclease activity that are capable of cleaving a single-stranded nucleic acid, such as an mRNA, that hybridizes to the ribozyme. Thus, ribozymes (e.g., hammerhead ribozymes (described in Haselhoff et al., Nature (1988) 334:585-591)) can be used to catalytically cleave nucleic acid transcripts and thus inhibit translation of mRNA corresponding to SEQ ID NO:1. A ribozyme having specificity for the nucleic acid of SEQ ID NO:1 can be designed based on the nucleotide sequence of SEQ ID NO:1. For example, a derivative of a Tetrahymena L-19 IVS RNA can be constructed so that the nucleotide sequence of the active site is complementary to the nucleotide sequence to be cleaved based on the reported nucleic acid sequence of SEQ ID NO:1 (U.S. Pat. Nos. 4,987,071 and 5,116,742, the disclosures of which are incorporated by reference). Alternatively, the nucleic acid sequence of SEQ ID NO:1 can be used to select a catalytic RNA having a specific ribonuclease activity from a pool of RNA molecules. (Bartel et al., Science (1993) 261:1411-1418.

Triple Helical Nucleic Acid Molecules and Peptide Nucleic Acids

The invention also encompasses nucleic acid molecules that form triple helical structures. For example, gene expression can be inhibited by targeting nucleotide sequences complementary to the regulatory region of SEQ ID NO:1 (e.g., the promoter and/or enhancer region) to form triple helical structures that prevent transcription of the gene in target cells, see generally, Helene, Anticancer Drug Des (1991) 6(6):569; Helene Ann NY Acad Sci (1992) 660:27; and Maher, Bioassays (1992) 14(12):807.

In particular embodiments, the nucleic acid molecules of the invention can be modified at the base moiety, sugar moiety or phosphate backbone to improve, e.g., the stability, hybridization or solubility of the molecule. For example, the deoxyribose phosphate backbone of the nucleic acids can be modified to generate peptide nucleic acids (see Hyrup et al., Bioorganic & Medicinal Chemistry (1996) 4:5). As used herein, the terms "peptide nucleic acids" or "PNAs" refer to nucleic acid mimics, e.g., DNA mimics, in that the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al., Proc Natl Acad Sci USA (1996) 93:14670.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs of the present invention also can be used. For example, a PNA can be used in the analysis of single base pair mutations in a gene by, e.g., PNA-directed PCR clamping; as artificial restriction enzymes when used in combination with other enzymes, e.g., S1 nucleases (Hyrup et al. (1996) supra) or as probes or primers for DNA sequence and hybridization (Hyrup et al. (1996) supra; Perry-O'Keefe et al. (1996) supra).

In another embodiment, PNAs of the present invention can be modified, e.g., to enhance stability, specificity or cellular uptake, by attaching lipophilic or other helper groups to the PNA, by the formation of PNA-DNA chimeras or by the use of liposomes or other techniques of drug delivery known in the art. The synthesis of PNA-DNA chimeras can be performed as described in Hyrup et al. (1996) supra, Finn et al., Nucleic Acids Res (1996) 24(17):3357-63, Mag et al., Nucleic Acids Res (1989) 17:5973; and Peterser et al., Bioorganic Med Chem Lett (1975) 5:1119.

RNA/Nucleic Acid Interference

RNA interference (RNAi) or nucleic acid interference (NAi) is a process of sequence-specific post-transcriptional gene silencing mediated by short interfering RNAs (siRNAs) or short interfering nucleic acids (siNA). This process is thought to be an evolutionarily conserved defense mechanism whereby the production of double-stranded RNAs (dsRNAs) or double stranded nucleic acids (dsNA), for instance as a result of viral infection, stimulates the activity of a ribonuclease III enzyme referred to as dicer (Berstein et al., 2001, Nature 409:363). For instance, Dicer processes the dsRNA into siRNA. Dicer may be involved in excising 21- and 22-nucleotide small temporal RNAs (siRNAs) implicated in translational control. The RNAi response also involves an endonuclease complex, an RNA-induced silencing complex (RISC), that cleaves target single-stranded RNA having sequence complementary to the antisense strand of the siRNA (Elbashir et al., 2001, Genes Dev., 15:188). Optimal design of siRNAs, dsRNAs, siNAs or dsNAs based on length, structure, chemical composition and sequence for efficient RNAi or NAi are known to those skilled in the art (for examples see: Chiu and Rana et al., 2003, RNA 9:1034-48; Elbashir et al., 2001; Parish et al., 2000; PCT Publication Nos., WO 03/070744, WO 01/75164, WO 01/68836, WO 01/49844, WO 01/36646, WO 01/29058, WO 00/44914 WO 00/01846, WO 99/32619,WO 99/07409 WO 99/53050; Canadian Patent Application No. 2,359,180, the disclosures of which are incorporated by reference). Some possible modifications to the siNA or dsNA to improve activity include but are not limited to: 3'-terminal dinucleotide overhangs, substitution of one or both siNA strands with 2'-deoxy nucleotides (2'-H), replacing the 3'-terminal nucleotide overhanging segments of the siNA duplex with deoxyribonucleotides, modifications to either the phosphate-sugar backbone or the nucleoside to include at least one of a nitrogen or sulfur heteroatom, 2'-amino or 2'-O-methyl nucleotides and nucleotides containing a 2'-O or 4'-C methylene bridge in dsRNA constructs, substituting 4-thiouracil, 5-bromouracil, 5-iodouracil and 3-(aminoallyl)uracil in sense and antisense strands. PCT Publication No. WO 01/68836 describes methods for using endogenously derived dsRNA to attenuate gene expression. Further, the mRNA targeted for RNAi has been suggested to act as a template for 5' to 3' synthesis of new dsRNA targeted to a gene in one cell type and can lead to RNAi-mediated silencing of a second gene expressed in a distinct cell type, a phenomenon termed transitive RNAi (Alder et al., 2003 rna 9:25).

Protein

The present invention extends to an isolated polypeptide comprising the amino acid sequence of SEQ ID NO:2, a variant thereof, a fragment thereof or an analog or derivative thereof.

An isolated nucleic acid molecule encoding a protein of the present invention having a sequence that differs from that of SEQ ID NO:2, e.g. a variant, can be created by introducing one or more nucleotide substitutions, additions or deletions into the nucleotide sequence of SEQ ID NO:1 such that one or more amino acid substitutions, additions or deletions are introduced into the encoded protein. For example, the first and third intracellular loops are three and five amino acids shorter in the guinea pig DP protein, respectively, whereas in the mouse, human and rat DP proteins these intracellular loops are all of identical size. A variant of SEQ ID NO:2 could be created be inserting one or more nucleotides found in any of the other orthologues.

In a particular embodiment, a mutant protein of the present invention can be assayed for: (1) the ability to form protein: protein interactions with proteins in the signaling pathway; (2) the ability to bind a ligand; (3) the ability to bind to an intracellular target protein, or (4) the ability to modulate cellular proliferation, cellular differentiation or cellular response.

Native proteins of the invention can be isolated from cells or tissue sources by an appropriate purification scheme using standard protein purification techniques. Alternatively, proteins of the invention can readily be produced by recombinant DNA techniques. Yet another alternative embodiment, is the chemical synthesis of the protein or the polypeptide of the invention using standard peptide synthesis techniques.

Biologically active portions or fragments of a protein of the invention include peptides comprising amino acid sequences sufficiently identical to or derived from the amino acid sequence of SEQ ID NO:2, that include fewer amino acids than the full length protein of the invention and exhibit at least one activity of the protein of the invention. Typically, biologically active portions comprise a domain or motif with at least one activity of the protein of the invention. For instance, a biologically active fragment of the protein of the invention could contain two sequence stretches that have previously been reported to be characteristically conserved amongst GPCRs of the prostanoid family (Hirata et al., 1994) and are also present in the guinea pig DP protein:

QYCPGTWCR (SEQ ID NO: 10) in the second extracellular loop and RFLSVISIVDPWIFI (SEQ ID NO: 11) in the seventh transmembrane domain. A biologically active portion of the protein of the invention can be a polypeptide that is, for example, 10, 25, 50, 100 or more amino acids in length. Particular biologically active polypeptides include one or more identified structural domains of the protein of the present invention. Moreover, other biologically active portions, in which other regions of the protein are deleted, can be prepared by recombinant techniques and evaluated for one or more of the functional activities of the protein of the invention. Further guidance directed to biologically relevant portion of the invention are provided below in "Example 3".

Other useful proteins are substantially identical to SEQ ID NO:2 and retain a functional activity of the protein of SEQ ID NO:2 yet differ in amino acid sequence due to natural allelic variation or mutagenesis. For example, such proteins and polypeptides possess at least one biological activity described herein. Accordingly, a useful protein of the invention is a protein that includes an amino acid sequence at least about 65%, 75%, 85%, 95%, 99% or 100% identical to the amino acid sequence of SEQ ID NO:2 and retains a functional activity of the protein of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions then are compared. When a position in the first sequence is occupied by the same amino acid residue or nucleotide as the corresponding position in the second sequence, then the molecules are considered identical at that position. The percent identity between the two sequences is a function of the number of identical positions shared by the sequences (i.e., percent identity=number of identical positions/total number of positions (e.g., overlapping positions)× 100). In one embodiment, the two sequences are the same length.

The determination of percent identity between two sequences can be accomplished using a mathematical algorithm. A particular, non-limiting example of a mathematical algorithm utilized for the comparison of two sequences is the algorithm of Karlin et al., Proc Natl Acad Sci USA (1990) 87:2264, modified as in Karlin et al., Proc Natl Acad Sci USA (1993) 90:5873-5877. Such an algorithm is incorporated into the NBLAST and XBLAST programs of Altschul et al., J Mol Bio (1990) 215:403. To obtain gapped alignments for comparison purposes, Gapped BLAST can be utilized as described in Altschul et al., Nucleic Acids Res (1997) 25:3389. Alternatively, PSI-Blast can be used to perform an iterated search that detects distant relationships between molecules. Altschul et al. (1997) supra. When utilizing BLAST, Gapped BLAST and PSI-Blast programs, the default parameters of the respective programs (e.g., XBLAST and NBLAST) can be used, see http://www.ncbi.nim.nih.gov. Another particular, non-limiting example of a mathematical algorithm utilized for the comparison of sequences is the algorithm of Myers et al., CABIOS (1988) 4:11-17. Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 may be used.

The percent identity between two sequences can be determined using techniques similar to those described above, with or without allowing gaps. In calculating percent identity, only exact matches are counted.

The present invention further extends to chimeric or fusion proteins of the invention. As used herein, a "chimeric protein" or "fusion protein" of the invention comprises a polypeptide of SEQ ID NO:2 operably linked to a "polypeptide not of the invention". A "polypeptide of the invention" refers to a polypeptide having an amino acid sequence corresponding to SEQ ID NO:2. A "polypeptide not of the invention" refers to a polypeptide having an amino acid sequence corresponding to a protein that is not substantially identical to SEQ ID NO:2, e.g., a protein that is different from the protein of the invention and is derived from the same or a different organism. Within a fusion protein of the invention, the polypeptide of the invention can correspond to all or a portion of a SEQ ID NO:2, preferably at least one biologically active portion of a SEQ ID NO:2. Within the fusion protein, the term "operably linked" is intended to indicate that the polypeptide of the invention and the polypeptide not of the invention are fused in-frame to each other. The polypeptide not of the invention can be fused to the N-terminus or C-terminus of the polypeptide of the invention. One useful fusion protein utilizes glutathione-S-transferase (GST) in which the polypeptide of the invention is fused to the C-terminus of GST. Such fusion proteins can facilitate the purification of recombinant polypeptides of the invention.

In another embodiment, a fusion protein of the present invention extends to an immunoglobulin fusion protein in that all or part of SEQ ID NO:2 is fused to sequences derived from a member of the immunoglobulin protein family. The immunoglobulin-fusion protein of the invention can be incorporated into pharmaceutical compositions and administered to a subject to inhibit an interaction between a ligand and the receptor protein of the invention on the surface of a cell, thereby to suppress receptor-mediated signal transduction in vivo. The immunoglobulin-fusion protein of the invention can be used to affect the bioavailability of a cognate ligand of the receptor of the present invention. Inhibition of the ligand-receptor interaction may be useful therapeutically, such as but not limited to, treating or modulating sleep, body temperature, olfactory function, hormone release, pain, gastrointestinal tract disorders, liver disease, eye diseases such as glaucoma, blood disorders such as thrombosis, inflammatory disorders including but not limited to asthma, allergic rhinitis, airway hyperactivity, allergic dermatitis, allergic conjunctivitis and chronic obstructive pulmonary disease. Moreover, the immunoglobulin-polypeptide fusion proteins of the invention can be used as immunogens to produce antibodies in a subject, to purify ligands and in screening assays to identify molecules that inhibit the interaction of the receptor of the invention with a ligand.

In a particular embodiment, a chimeric or fusion protein of the present invention is produced by standard recombinant DNA techniques. For example, DNA fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that subsequently can be annealed and reamplified to generate a chimeric gene sequence (see e.g., Ausubel et al., supra). Moreover, many expression vectors are commercially available that already encode a fusion moiety (e.g., a GST polypeptide). A nucleic acid encoding the polypeptide of the invention or a portion thereof can be cloned into such an expression vector so that the fusion moiety is linked in-frame to the protein of the invention.

Nucleic Acid and Protein Variants

As explained above, the present invention further extends to variants of SEQ ID NO:1 and SEQ ID NO:2. For example, mutations may be introduced into the amino acid sequence of SEQ ID NO:1 using standard techniques, such as site-directed mutagenesis and PCR-mediated mutagenesis. Moreover, conservative amino acid substitutions can be made at one or more predicted non-essential amino acid residues. A "conservative amino acid substitution" is one in which the amino acid residue is replaced with an amino acid residue having a similar side chain. For example, one or more amino acids can be substituted by another amino acid of a similar polarity, which acts as a functional equivalent, resulting in a silent alteration. Substitutes for an amino acid within the amino acid sequence of a polypeptide of the present invention may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to effect apparent molecular weight as determined by polyacrylamide gel electrophoresis, or isoelectric point.

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Additional substitutions may be made with synthetic (i.e., non-naturally occurring) amino acids.

Amino acid substitutions may also be introduced to substitute an amino acid with a particularly preferable property. For example, a Cys may be introduced for a potential site for disulfide bridges with another Cys. A H may be introduced as a particularly "catalytic" site (i.e., His can act as an acid or base and is the most common amino acid in biochemical catalysis). Pro may be introduced because of its particularly planar structure, which induces β-turns in the protein's structure.

Mutations can also be introduced randomly along all or part of a coding sequence of SEQ ID NO:1, such as by saturation mutagenesis, and the resultant mutants can be screened for biological activity to identify mutants that retain activity. Following mutagenesis, the encoded protein can be expressed recombinantly and the activity of the protein can be determined.

Variants of the present invention can function as an agonist (mimetic) or as an antagonist. Variants of the protein of the invention can be generated by mutagenesis, e.g., discrete point mutation or truncation of the protein of the invention. An agonist of the protein of the invention can retain substantially the same or a subset of the biological activities of the naturally occurring protein of the invention. An antagonist can competitively bind to a downstream or upstream member of a cellular signaling cascade that includes the protein of the invention, and thus inhibit one or more of the activities of the naturally occurring form of the protein of the invention. Thus, specific biological effects can be elicited by treatment with a variant of limited function. Treatment of a subject with a variant having a subset of the biological activities of the naturally occurring form of the protein of the invention can have fewer side effects in a subject relative to treatment with the naturally occurring form of the protein.

Variants of the protein of the invention that function as either agonists (mimetics) or as antagonists can be identified by screening combinatorial libraries of mutants, e.g., truncation mutants, of the protein of the invention for agonist or antagonist activity. In one embodiment, a variegated library of variants of the protein of the invention are generated by combinatorial mutagenesis at the nucleic acid level, and is encoded by a variegated gene library. A variegated library of variants can be produced by, for example, enzymatically ligating a mixture of synthetic oligonucleotides into gene sequences such that a degenerate set of potential nucleic acid sequences of the invention are expressed as individual polypeptides or alternatively, as a set of larger fusion proteins (e.g., for phage display) containing the set of sequences of the invention therein. There are a variety of methods that can be used to produce libraries of potential variants of the invention from a degenerate oligonucleotide sequence. Chemical synthesis of a degenerate gene sequence can be performed in an automated DNA synthesizer and the synthetic gene then ligated into an appropriate expression vector. Use of a degenerate set of genes allows for the provision, in one mixture, of all of the sequences encoding the desired set of potential nucleic acid sequences of the invention. Methods for synthesizing degenerate oligonucleotides are known in the art (see, e.g., Narang, Tetrahedron (1983) 39:3; Itakura et al., Ann Rev Biochem (1984) 53:323; Itakura et al., Science (1984) 198: 1056; Ike et al., Nucleic Acid Res (1983) 11:477).

In addition, libraries of fragments of the protein coding sequence can be used to generate a variegated population of fragments for screening and subsequent selection of variants of a protein of the invention. In one embodiment, a library of coding sequence fragments can be generated by treating a double-stranded PCR fragment of a coding sequence of the invention with a nuclease under conditions wherein nicking occurs only about once per molecule, denaturing the double-stranded DNA, renaturing the DNA to form double-stranded DNA that can include sense/antisense pairs from different nicked products, removing single-stranded portions from reformed duplexes by treatment with S1 nuclease and ligating the resulting fragment library into an expression vector. By that method, an expression library can be derived that encodes N-terminal and internal fragments of various sizes of the protein of the invention.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of the protein of the invention. The most widely used techniques that are amenable to high through-put analysis for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify variant proteins of the invention (Arkin et al., Proc Natl Acad Sci USA (1992) 89:7811-7815; Delgrave et al., Protein Engineering (1993) 6(3):327-331).

Analogs and Derivatives of the Protein of the Invention

Moreover, the present invention also includes derivatives or analogs of the protein of the invention produced from a chemical modification. A protein of the present invention may be derivatized by the attachment of one or more chemical moieties to the protein moiety.

The chemical moieties suitable for derivatization may be selected from among water soluble polymers so that the analog or derivative does not precipitate in an aqueous environment, such as a physiological environment. Optionally, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the protein of the invention, these may be ascertained using the assays provided herein. Examples of water soluble polymers having applications herein include, but are not limited to, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran, poly(-vinyl pyrrolidone)polyethylene glycol, propropylene glycol homopolymers, polypropylene oxide/ethylene oxide co-polymers, polyoxyethylated polyols or polyvinyl alcohol. Polyethylene glycol propionaldehyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects if any, on biological activity, the ease in handling, the degree or lack of antigenicity and other known effects of the polyethylene glycol to a therapeutic protein or analog).

The number of polymer molecules so attached to the protein of the invention may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein molecules of the invention will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein of the invention with consideration of effects on functional or antigenic domains. There are a number of attachment methods available to those skilled in the art, e.g., EP 0401384 herein incorporated by reference (coupling PEG to G-CSF), see also Malik et al., 1992, Exp. Hematol. 20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the N-terminal amino acid residues; those having a free carboxyl group include aspartic acid residues, glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group.

One may specifically desire a N-terminally chemically modified protein of the invention. Using polyethylene glycol as an illustration of the present compositions, one may select from a variety of polyethylene glycol molecules (by molecular weight, branching, etc.), the proportion of polyethylene glycol molecules to protein molecules of the invention in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization. Under the appropriate reaction conditions, substantially selective derivatization at the N-terminus with a carbonyl group containing polymer is achieved. For example, one may selectively N-terminally pegylate the protein of the invention by performing the reaction at a pH which allows one to take advantage of the $pK_a$ differences between the ϵ-amino groups of the lysine residues and that of the α-amino group of the N-terminal residue. By such selective derivatization, attachment of a water soluble polymer to the protein of the invention is controlled: the conjugation with the polymer takes place predominantly at the N-terminus and no significant modification of other reactive groups, such as the lysine side chain amino groups, occurs. Using reductive alkylation, the water soluble polymer may be of the type described above, and should have a single reactive aldehyde for coupling to the protein of the invention. Polyethylene glycol proprionaldehyde, containing a single reactive aldehyde, may be used.

Antibodies

An isolated protein of the invention or a portion or fragment thereof, can be used as an immunogen to generate antibodies that bind the protein of the invention using standard techniques for polyclonal and monoclonal antibody preparation. The term "antibody" as used herein refers to immunoglobulin molecules and immunologically active portions of immunoglobulin molecules, i.e., molecules that contain an antigen-binding site that is specific for—that is, that binds to—an antigen, such as the protein of the invention, or a fragment thereof. A molecule that specifically binds to the protein of the invention is a molecule that binds the protein of the invention, but does not substantially bind other molecules in a sample, e.g., a biological sample that naturally contains the protein of the invention. Examples of immunologically active portions of immunoglobulin molecules include $F_{(ab)}$ and $F_{(ab')2}$ fragments that can be generated by treating the antibody with an enzyme such as pepsin. The invention provides polyclonal, monoclonal and chimeric antibodies that have the protein of the invention, a variant thereof, a fragment thereof, or an analog or derivative thereof, as an immunogen. Chimeric antibodies are preferred for use in therapy of human diseases or disorders, since the human or humanized antibodies are much less likely than xenogenic antibodies to induce an immune response, in particular an allergic response, themselves.

The full-length protein of the invention can be used or, alternatively, the invention provides antigenic peptide fragments of the invention for use as immunogens. The antigenic peptide of the invention comprises at least 8 (preferably 10, 15, 20, 30 or more) amino acid residues of the amino acid sequence shown in SEQ ID NO:2 and encompasses an epitope such that an antibody raised against the peptide forms a specific immune complex with the protein of the invention.

An immunogen typically is used to prepare antibodies by immunizing a suitable subject, (e.g., rabbit, goat, mouse or other mammal) with the immunogen. An appropriate immunogenic preparation can contain, for example, recombinantly expressed protein of the invention or a chemically synthesized polypeptide of the invention. The preparation further can include an adjuvant, such as Freund's complete or incomplete adjuvant or similar immunostimulatory agent. Immunization of a suitable subject with an immunogenic preparation induces a polyclonal antibody response directed against the protein of the invention.

An antibody of the present invention can be a monoclonal antibody, a polyclonal antibody, or a chimeric antibody. The term "monoclonal antibody" or "monoclonal antibody composition", as used herein, refers to a population of antibody molecules that contain only one species of an antigen-binding site capable of immunoreacting with a particular epitope of the protein of the invention. A monoclonal antibody composition thus typically displays a single binding affinity for a particular epitope of the protein of the invention.

Polyclonal antibodies can be prepared as described above by immunizing a suitable subject with an immunogen of the invention. The antibody titer in the immunized subject can be monitored over time by standard techniques, such as with an enzyme-linked immunosorbent assay (ELISA) using the protein of the invention that has been immobilized. If desired, the antibody molecules directed against the protein of the invention can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler et al., Nature (1975) 256:495-497, the human B cell hybridoma technique (Kohler et al., Immunol Today (1983) 4:72), the EBV hybridoma technique (Cole et al., Monoclonal Antibodies and Cancer Therapy, (1985), Alan R. Liss, Inc., pp. 77-96) or trioma techniques. The technology for producing hybridomas is well known (see generally Current Protocols in Immunology (1994) Coligan et al., eds., John Wiley & Sons, Inc., New York, N.Y.). Briefly, an immortal cell line (typically a myeloma) is fused to lymphocytes (typically splenocytes) from a mammal immunized with an immunogen of the invention as described above and the culture supernatants of the resulting hybridoma cells are screened to identify a hybridoma producing a monoclonal antibody that binds the protein of the invention.

Any of the many well known protocols used for fusing lymphocytes and immortalized cell lines can be applied for the purpose of generating a monoclonal antibody (see, e.g., Current Protocols in Immunology, supra; Galfre et al., Nature (1977) 266:550-552; Kenneth, in Monoclonal Antibodies: A New Dimension In Biological Analyses, Plenum Publishing Corp., New York, N.Y. (1980); and Lerner, Yale J Biol Med (1981) 54:387-402). Moreover, the ordinarily skilled worker will appreciate that there are many variations of such methods that also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/I-Ag4-1, P3-x63-Ag8.653 or Sp2/O-Agl4 myeloma lines. The myeloma lines are available from ATCC. Typically, HAT-sensitive mouse myeloma cells are fused to mouse splenocytes using polyethylene glycol ("PEG"). Hybridoma cells resulting from the fusion then are selected using HAT medium that kills unfused and unproductively fused myeloma cells (unfused splenocytes die after several days because they are not transformed). Hybridoma cells producing a monoclonal antibody of the invention are detected by screening the hybridoma culture supernatants for antibodies that bind the protein of the invention, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the protein of the invention thereby to isolate immunoglobulin library members that bind the protein of the invention. Kits for generating and screening phage display libraries are commercially available (e.g., the Pharmacia Recombinant Phage Antibody System, Catalog No. 27-9400-01; and the Stratagene "SURFZAP" Phage Display Kit, Catalog No. 240612).

Additionally, examples of methods and reagents particularly amenable for use in generating and screening antibody display libraries are known to those skilled in the art. (for example, Fuchs et al., Bio/Technology (1991)9:1370 1372; Hay et al., Hum Antibody Hybridomas (1992) 3:81 85; Huse et al., Science (1989) 246:1275-1281; Griffiths et al., EMBO J. (1993) 25(12):725-734; U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809, the disclosures of which are incorporated by reference).

Furthermore, recombinant antibodies, such as chimeric and humanized monoclonal antibodies comprising both human and non-human portions, can be made using standard recombinant DNA techniques. Such chimeric and humanized monoclonal antibodies can be produced by recombinant DNA techniques known in the art (for example using methods described in PCT Publication No. WO 87/02671; Europe Patent Application No. 184,187; Europe Patent Application No. 171,496; Europe Patent Application No. 173,494; PCT Publication No. WO 86/01533; U.S. Pat. No. 4,816,567; Europe Patent Application No. 125,023; Better et al., Science (1988) 240:1041-1043; Liu et al., Proc Natl Acad Sci USA (1987) 84:3439-3443; Lin et al., J Immunol (1987) 139:3521-3526; Sun et al., Proc Natl Acad Sci USA (1987) 84:214-218; Nishimura et al., Canc Res (1987) 47:999-1005; Wood et al., Nature (1985) 314:446-449; Shaw et al., J Natl Cancer Inst (1988) 80:1553-1559; Morrison, Science (1985) 229:1202-1207; Oi et al., Bio/Techniques (1986) 4:214; U.S. Pat. No. 5,225,539; Jones et al., Nature (1986) 321:552-525; Verhoeyan et al., Science (1988) 239:1534; and Beidler et al., J Immunol (1988) 141:4053-4060; the disclosures of which are incorporated by reference).

Completely human antibodies are particularly desirable for therapeutic treatment of human patients. Such antibodies can be produced using transgenic mice that are incapable of expressing endogenous immunoglobulin heavy and light chains genes, but can express human heavy and light chain genes. The transgenic mice are immunized in the normal fashion with a selected antigen, e.g., all or a portion of the protein of the invention. Monoclonal antibodies directed against the antigen can be obtained using conventional hybridoma technology. The human immunoglobulin transgenes harbored by the transgenic mice rearrange during B cell differentiation and subsequently undergo class switching and somatic mutation. Thus, using such an epitope, e.g., an antibody that inhibits the activity of the protein of the invention is identified. The heavy chain and the light chain of the non-human antibody are cloned and used to create phage display $F_{ab}$ fragments. For example, the heavy chain gene can be cloned into a plasmid vector so that the heavy chain can be secreted from bacteria. The light chain gene can be cloned into a phage coat protein gene so that the light chain can be expressed on the surface of phage. A repertoire (random collection) of human light chains fused to phage is used to infect the bacteria that express the non-human heavy chain. The resulting progeny phage display hybrid antibodies (human light chain/non-human heavy chain). The selected antigen is used in a panning screen to select phage that bind the selected antigen. Several rounds of selection may be required to identify such phage.

Human light chain genes are isolated from the selected phage that bind the selected antigen. The selected human light chain genes then are used to guide the selection of human heavy chain genes as follows. The selected human light chain genes are inserted into vectors for expression by bacteria. Bacteria expressing the selected human light chains are infected with a repertoire of human heavy chains fused to phage. The resulting progeny phage display human antibodies (human light chain/human heavy chain).

Next, the selected antigen is used in a panning screen to select phage that bind the selected antigen. The selected phage display a completely human antibody that recognizes the same epitope recognized by the original selected, non-human monoclonal antibody. The genes encoding both the heavy and light chains are isolated and can be manipulated further for production of human antibody. The technology is described by Jespers et al. (Bio/Technology (1994) 12:899-903).

An antibody (e.g., monoclonal antibody) can be used to isolate the protein of the invention by standard techniques, such as affinity chromatography or immunoprecipitation. An antibody directed against the protein of the invention can facilitate the purification of the natural protein from cells and of recombinantly produced protein expressed in host cells. Moreover, an antibody can be used to detect the protein of the invention (e.g., in a cellular lysate or cell supernatant) to evaluate the abundance and pattern of expression of the protein. Antibodies can be used diagnostically to monitor protein levels in tissue as part of a clinical testing procedure, for example, to determine the efficacy of a given treatment regimen. Detection can be facilitated by coupling the antibody to a detectable substance, which are described infra.

Detectable Labels

Optionally, isolated nucleic acid molecules of the present invention, polypeptides of the present invention, and antibodies of the present invention, as well as fragments of such moieties, may be detectably labeled. Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), bioluminescent materials, and chemiluminescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of detectable labels that can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No.

4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme immunoassay ELISA and EMIT in *Methods in Enzymology*, 70. 419-439, 1980 and in U.S. Pat. No. 4,857,453.

Other detectable labels for use in the invention include magnetic beads or magnetic resonance imaging labels.

In another embodiment, a phosphorylation site can be created on an isolated polypeptide of the present invention, an antibody of the present invention, or a fragment thereof, for labeling with $^{32}$P, e.g., as described in European Patent No. 0372707.

As exemplified herein, proteins, including antibodies, can be detectably labeled by metabolic labeling. Metabolic labeling occurs during in vitro incubation of the cells that express the protein in the presence of culture medium supplemented with a metabolic label, such as [$^{35}$S]-methionine or [$^{32}$P]-orthphosphate. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Antibodies may further be detected using, in addition to the label recited above, antigenic peptide tags recognizable by antibodies. Examples include HA tags and FLAG® tags.

Recombinant Expression Vectors and Host Cells

Another aspect of the invention pertains to vectors, preferably expression vectors, containing a nucleic acid encoding SEQ ID NO:1 or a portion thereof. As explained above, one type of vector is a "plasmid," which refers to a circular double-stranded DNA loop into which additional DNA segments can be ligated. Another type of vector is a viral vector, wherein additional DNA segments can be ligated into a viral genome. Certain vectors are capable of autonomous replication in a host cell (e.g., bacterial vectors having a bacterial origin of replication and episomal mammalian vectors). Other vectors (e.g., non-episomal mammalian vectors) are integrated into the genome of a host cell on introduction into the host cell and thereby are replicated along with the host genome. Moreover, expression vectors are capable of directing the expression of genes operably linked thereto. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), that serve equivalent functions.

A recombinant expression vector of the invention comprises a nucleic acid molecule of the present invention in a form suitable for expression of the nucleic acid in a host cell. That means a recombinant expression vector of the present invention includes one or more regulatory sequences, selected on the basis of the host cells to be used for expression, that is operably linked to the nucleic acid to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology Vol. 185, Academic Press, San Diego, Calif. (1990). Regulatory sequences include those that direct constitutive expression of the nucleotide sequence in many types of host cells (e.g., tissue specific regulatory sequences). It will be appreciated by those skilled in the art that the design of the expression vector can depend on such factors as the choice of host cell to be transformed, the level of expression of protein desired etc. The expression vectors of the invention can be introduced into host cells to produce proteins or peptides encoded by nucleic acids as described herein A recombinant expression vector of the invention can be designed for expression of SEQ ID NO:1 or a portion thereof in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using phage regulatory elements and proteins, such as, a T7 promoter and/or a T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes and the cognate recognition sequences, include Factor Xa, thrombin and enterokinase. Typical fusion expression vectors include pGEX (Pharmacia Biotech Inc; Smith et al., Gene (1988) 67:31-40), pMAL (New England Biolabs, Beverly, Mass.) and pRITS (Pharmacia, Piscataway, N.J.), that fuse glutathione 5-transferase (GST), maltose E binding protein or protein A, respectively, to the target recombinant protein.

Examples of suitable inducible non-fusion *E. coli* expression vectors include pTrc (Amann et al., Gene (1988) 69:301-315) and pET 11d (Studier et al., Gene Expression Technology: Methods in Enzymology, Academic Press, San Diego, Calif. (1990) 185:60-89). Target gene expression from the pTrc vector relies on host RNA polymerase transcription from a hybrid trp-lac fusion promoter.

One strategy to maximize recombinant protein expression in *E. coli* is to express the protein in a host with impaired capacity to cleave proteolytically the recombinant protein (Gottesman, Gene Expression Technology: Methods in Enzymology, Academic Press, San Diego, Calif. (1990) 185:119-128). Another strategy is to alter the nucleic acid sequence of the nucleic acid molecule to be inserted into an expression vector so that the individual codons for each amino acid are those preferentially utilized in *E. coli* (Wada et al., Nucleic Acids Res (1992) 20:2111-2118). Such alteration of nucleic acid sequences of the invention can be carried out by standard DNA synthesis techniques.

In another embodiment, the expression vector of the invention is a yeast expression vector. Examples of vectors for expression in yeast such as *S. cerevisiae* include pYepSecI (Baldari et al., EMBO J. (1987) 6:229-234), pMFa (Kurjan et al., Cell (1982) 30:933-943), pJRY88 (Schultz et al., Gene (1987) 54:113-123), pYES2 (Invitrogen Corporation, San Diego, Calif.) and pPicZ (Invitrogen Corp, San Diego, Calif.).

Alternatively, SEQ ID NO:1 or a portion thereof can be expressed in insect cells using baculovirus expression vectors. Baculovirus vectors available for expression of proteins in cultured insect cells (e.g., Sf 9 cells) include the pAc series (Smith et al., Mol Cell Biol (1983) 3:2156-2165) and the pVL series (Lucklow et al., Virology (1989) 170:31-39).

In yet another embodiment, a nucleic acid of the invention is expressed in mammalian cells using a mammalian expression vector. Examples of mammalian expression vectors having applications herein include, but certainly are not limited to pCDM8 (Seed, Nature (1987) 329:840) and pMT2PC (Kaufman et al., EMBO J. (1987) 6:187-195). When used in mammalian cells, control functions of the expression vector often are provided by viral regulatory elements. For example, commonly used promoters are derived from polyoma, adenovirus 2, cytomegalovirus and simian virus 40. For other suitable expression systems for both prokaryotic and eukaryotic cells, see chapters 16 and 17 of Sambrook et al., supra.

In another embodiment, a recombinant mammalian expression vector of the present invention is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., Genes Dev (1987) 1:268-277), lymphoid-specific promoters (Calame et al., Adv Immunol (1988) 43:235-275), in particular, promoters of T cell receptors (Winoto et al., EMBO J (1989) 8:729-733) and immunoglobulins (Banerji et al., Cell (1983) 33:729-740; Queen et al., Cell (1983) 33:741-748), neuron-specific promoters (e.g., the neurofilament promoter; Byrne et al., Proc Natl Acad Sci USA (1989) 86:5473-5477), pancreas-specific promoters (Edlund et al., Science (1985) 230:912-916) and mammary gland-specific promoters (e.g., milk whey promoter; U.S. Pat. No. 4,873,316 and Europe Application No. 264,166). Developmentally-regulated promoters also are encompassed, for example the murine hox promoters (Kessel et al., Science (1990) 249:374-379) and the α-fetoprotein promoter (Campes et al., Genes Dev (1989) 3:537-546). The disclosures of each of the foregoing references are incorporated herein by reference.

The invention further provides a recombinant expression vector comprising a DNA molecule of the invention cloned into an expression vector in an antisense orientation. That is, the DNA molecule is operably linked to a regulatory sequence in a manner that allows for expression (by transcription of the DNA molecule) of an RNA molecule that is antisense to mRNA of the invention. Regulatory sequences operably linked to a nucleic acid cloned in the antisense orientation can be chosen that direct the continuous expression of the antisense RNA molecule in a variety of cell types. For example, viral promoters and/or enhancers or regulatory sequences can be chosen that direct constitutive, tissue-specific or cell type-specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (Reviews-Trends in Genetics, Vol. 1(1)1986).

Another aspect of the present invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but still are included within the scope of the term as used herein.

A host cell can be any prokaryotic or eukaryotic cell. For example, the protein of the invention can be expressed in bacterial cells such as *E. coli*, insect cells, yeast or mammalian cells (such as Chinese hamster ovary cells (CHO), 293 cells or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, transduction, DEAE-dextran-mediated transfection, lipofection or electroporation.

For stable transfection of mammalian cells, it is known that, depending on the expression vector and transfection technique used, only a small fraction of cells may integrate the foreign DNA into the genome. To identify and to select the integrants, a gene that encodes a selectable marker (e.g., for resistance to antibiotics) generally is introduced into the host cells along with the gene of interest. Preferred selectable markers include those that confer resistance to drugs, such as G418, hygromycin and methotrexate. Nucleic acid encoding a selectable marker can be introduced into a host cell on the same vector as that encoding SEQ ID NO:1 or a portion thereof or the nucleic acid encoding a selectable marker can be introduced on a separate vector. For example, cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the protein of the invention. Accordingly, the invention further provides methods for producing SEQ ID NO:2 or a portion thereof by using the host cells of the invention. In one embodiment, the method comprises culturing the host cell of invention (into which a recombinant expression vector encoding SEQ ID NO:1 has been introduced) in a suitable medium such that the protein of the invention is produced. In another embodiment, the method further comprises isolating the protein of the invention from the medium or the host cell.

In another embodiment, the invention comprises an inducible expression system for the recombinant expression of other proteins subcloned in modified expression vectors. For example, host cells comprising a mutated G protein (e.g., yeast cells, Y2 adrenocortical cells and cyc⁻ S49, see U.S. Pat. Nos. 6,168,927 B1, 5,739,029 and 5,482,835; Mitchell et al., Proc Natl Acad Sci USA (1992) 89(19):8933-37 and Katada et al., J Biol Chem (1984) 259(6):3586-95) are transduced with a first expression vector comprising a nucleic acid sequence encoding SEQ ID NO:1, wherein SEQ ID NO:2 is functionally expressed in the host cells. Even though the expressed protein of the invention is constitutively active, the mutation does not allow for signal transduction; i.e., no activation of a G-protein directed downstream cascade occurs (e.g., no adenylyl cyclase activation). Subsequently, a second expression vector is used to transduce the SEQ ID NO:1-comprising host cells. The second vector comprises a structural gene that complements the G protein mutation of the host cell (i.e., functional mammalian or yeast $G_s$, $G_i$, $G_o$, or $G_q$, e.g., see PCT Publication No. WO 97/48820; U.S. Pat. Nos. 6,168,927 B1, 5,739,029 and 5,482,835 and which are hereby incorporated by reference herein in their entireties) in addition to the gene of interest to be expressed by the inducible system. The complementary structural gene of the second vector is inducible; i.e., under the control of an exogenously added component (e.g., tetracycline, IPTG, small molecules etc., see Sambrook et al. supra) that activates a promoter which is operably linked to the complementary structural gene. On addition of the inducer, the protein encoded by the complementary structural gene is functionally expressed such that the constitutively active protein of the invention now will form a complex that leads to appropriate downstream pathway activation (e.g., second messenger formation). The gene of interest comprising the second vector possesses an operably linked promoter that is activated by the appropriate second messenger (e.g., CREB, AP1 elements). Thus, as second messenger accumulates, the promoter upstream from the gene of interest is activated to express the product of said gene. When the inducer is absent, expression of the gene of interest is switched off.

In a particular embodiment, the host cells for the inducible expression system include, but are not limited to, S49 (cyc⁻) cells. While cell lines are contemplated that comprise G-protein mutations, suitable mutants may be artificially produced/constructed (see U.S. Pat. Nos. 6,168,927 B1, 5,739,029 and 5,482,835 for yeast cells).

In a related aspect, the cells are transfected with a vector operably linked to a cDNA comprising a sequence encoding a protein as set forth in SEQ ID NO:2. The first and second vectors comprising said system are contemplated to include, but are not limited to, pCDM8 (Seed, Nature (1987) 329:840) and pMT2PC (Kaufman et al., EMBO J (1987) 6:187-195), pYepSec1 (Baldari et al., EMBO J (1987) 6:229-234), pMFa (Kurjan et al., Cell (1982) 30:933-943), pJRY88 (Schultz et al., Gene (1987) 54:113-123), pYES2 (Invitrogen Corporation, San Diego, Calif.) and pPicZ (Invitrogen Corp, San Diego, Calif.).

In a related aspect, the host cells may be transfected by such suitable means, wherein transfection results in the expression of a functional protein (e.g., Sambrook et al., supra, and Kriegler, Gene Transfer and Expression: A Laboratory Manual, Stockton Press, New York, N.Y., 1990). Such "functional proteins" include, but are not limited to, proteins that once expressed, form complexes with G-proteins, where the G-proteins regulate second messenger formation. Other methods for transfecting host cells that have applications herein include, but certainly are not limited to transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

A large variety of promoters have applications in the present invention. Indeed, expression of a polypeptide of the present invention may be controlled by any promoter/enhancer element known in the art, but these regulatory elements must be functional in the host selected for expression. Promoters which may be used to control expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Expression vectors containing a nucleic acid molecule of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding the protein of the invention, a variant thereof, or an analog or derivative thereof, is inserted within the "selection marker"

gene sequence of the vector, recombinants containing the insert can be identified by the absence of the gene function. In the fourth approach, recombinant expression vectors can be identified by assaying for the activity, biochemical, or immunological characteristics of the gene product expressed by the recombinant vector, provided that the expressed protein assumes a functionally active conformation.

A wide variety of host/expression vector combinations may be employed in expressing the DNA sequences of this invention. Useful expression vectors may consist, for example, of segments of chromosomal, non-chromosomal and synthetic DNA sequences. Suitable vectors include derivatives of SV40 and known bacterial plasmids, e.g., *E. coli* plasmids col EI, pCR1, pBR322, pMal-C2, pET, pGEX (Smith et al., 1988, Gene 67:31-40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, Bg/II, and PstI cloning site; Invitrogen), pVL1392 (Bg/II, PstI, NotI, XmaIII, EcoRI, XbaI, SmaI, and BamH1 cloning site; Summers and Invitrogen), and pBlueBacIII (BamH1, Bg/II, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, Bg/II, PstI, NcoI, and HindIII cloning site, an N-terminal peptide for ProBond purification, and blue/white recombinant screening of plaques; Invitrogen (220) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and Bc/I cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible metallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (Sa/I, SmaI, Af/I, NarI, BspMII, BamHI, ApaI, NheI, SacII, KpnI, and HindIII cloning site; TK- and β-gal selection), and pTKgptF1S (EcoRI, PstI, Sa/I, AccI, HindII, SbaI, BamHI, and Hpa cloning site, TK or XPRT selection).

Yeast expression systems can also be used according to the invention to express the protein of the invention, a variant thereof, or an analog or derivative thereof. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors that can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen that modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce a nonglycosylated core protein product.

Transgenic Animals

A host cell of the present invention also can be used to produce nonhuman transgenic animals. For example, in one embodiment, a host cell of the invention is a fertilized oocyte or an embryonic stem cell into which sequences corresponding to SEQ ID NO:1 have been introduced. Such host cells then can be used to create non-human transgenic animals into which the exogenous sequences have been introduced into the genome, or homologous recombinant animals in which endogenous sequences have been altered. Such animals are useful for studying the function and/or activity of the protein of the invention and for identifying and/or evaluating modulators of the protein of the invention's activity. As used herein, a "transgenic animal" is a non-human animal, preferably a mammal, more preferably a rodent such as a rat or mouse, in that one or more of the cells of the animal includes a transgene. Other examples of transgenic animals include nonhuman primates, sheep, dogs, cows, goats, chickens, amphibians etc. A particular embodiment of the invention is a guinea pig that overexpresses the receptor of the invention and would have utility as an animal model of allergic rhinitis, bronchial asthma or chronic obstructive pulmonary disease.

As used herein, the term "transgene" refers to exogenous DNA that is integrated into the genome of a cell from which a transgenic animal develops and that remains in the genome of the mature animal. The transgene directs the expression of an encoded gene product in one or more cell types or tissues of the transgenic animal. As used herein, a "homologous recombinant animal" is a non-human animal, preferably a mammal, more preferably a mouse, in which an endogenous gene corresponding to SEQ ID. NO:1 has been altered by homologous recombination. That is accomplished between the endogenous gene and an exogenous DNA molecule introduced into a cell of the animal, e.g., an embryonic cell of the animal, prior to development of the animal.

A transgenic animal of the invention can be created by introducing a nucleic acid molecule encoding SEQ ID NO:1 or a portion thereof into the male pronuclei of a fertilized oocyte using one of the transfection methods described above. The oocyte is then allowed to develop in a pseudopregnant female foster animal. The cDNA sequence e.g., that of (SEQ ID NO: I), for example, can be introduced as a transgene into the genome of a non-human animal. Alternatively, a nonhuman homologue of the human gene, such as a mouse gene, can be isolated based on hybridization to the cDNA corresponding to SEQ ID NO:1, and used as a transgene. Intronic sequences and polyadenylation signals also can be included in the transgene to increase the efficiency of expression of the transgene. A tissue-specific regulatory sequence(s) can be operably linked to the transgene of the invention to direct expression of the protein of the invention in particular cells. Methods for generating transgenic animals via embryo manipulation and microinjection, particularly animals such as mice, are conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986), the disclosures of each of which are incorporated herein by reference. Similar methods are used for production of other transgenic animals with a transgene in the genome and/or expression of mRNA of the invention in tissues or cells of the animals. A transgenic founder animal then can be used to breed additional animals carrying the transgene. Moreover, transgenic animals carrying a transgene encoding SEQ ID NO:1 can be bred further to other transgenic animals carrying other transgenes.

To create a homologous recombinant animal, a vector is prepared that contains at least a portion of the gene of the invention (e.g., a human or a non-human homolog of the gene of the invention, e.g., a murine gene) into which a deletion, addition or substitution has been introduced thereby to alter, e.g., functionally disrupt, the gene of the invention. In a particular embodiment, the vector is designed such that, on homologous recombination, the endogenous gene is disrupted functionally (i.e., no longer encodes a functional protein; also referred to as a "knock out" vector).

Alternatively, the vector can be designed such that, on homologous recombination, the endogenous gene is mutated or otherwise altered but still encodes functional protein (e.g., an upstream regulatory region can be altered thereby altering the expression of the endogenous protein).

In the homologous recombination vector, the altered portion of the gene is flanked at the 5' and 3' ends by an additional nucleic acid sequence of the gene to allow for homologous recombination to occur between the exogenous gene carried by the vector and an endogenous gene in an embryonic stem cell. The additional flanking nucleic acid sequence is of sufficient length for successful homologous recombination with the endogenous gene. Typically, several kilobases of flanking DNA (both at the 5' and 3' ends) are included in the vector (see, e.g., Thomas et al., Cell (1987) 51:503 for a description of homologous recombination vectors).

The vector is introduced into an embryonic stem cell line (e.g., by electroporation) and cells in which the introduced gene of the invention has homologously recombined with the endogenous gene are selected (see, e.g., Li et al., Cell (1992) 69:915). The selected cells then are injected into a blastocyst of an animal (e.g., a mouse) to form aggregation chimeras (see, e.g., Bradley in Teratocarcinomas and Embryonic Stem Cells: A Practical Approach, Robertson, ed., IRL, Oxford, (1987) pp. 113-152). A chimeric embryo then can be implanted into a suitable pseudopregnant female foster animal and the embryo brought to term. Progeny harboring the homologously recombined DNA in the germ cells can be used to breed animals in that all cells of the animal contain the homologously recombined DNA by germline transmission of the transgene.

Methods for constructing homologous recombination vectors and homologous recombinant animals are described further in Bradley, Current Opinion in Bio/Technology (1991) 2:823-829 and in PCT Publication Nos. WO 90/11354, WO 91/01140, WO 92/0968 and WO 93/04169, the disclosures of which are incorporated by reference.

In another embodiment, transgenic non-human animals can be produced that contain selected systems to allow for regulated expression of the transgene. One example of such a system is the cre/loxP recombinase system of bacteriophage P1. For a description of the cre/loxP recombinase system, see, e.g., Lakso et al., Proc Natl Acad Sci USA (1992) 89:6232-6236. Another example of a recombinase system is the FLP recombinase system of S. cerevisiae (O'Gorman et al., Science (1991) 251:1351-1355). If a cre/loxP recombinase system is used to regulate expression of the transgene, animals containing transgenes encoding both the cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein also can be produced according to the methods described in Wilmut et al., Nature (1997) 385:810-813 and PCT Publication Nos. WO 97/07668 and WO 97/07669 (and which are hereby incorporated by reference herein in their entireties). In brief, a cell, e.g., a somatic cell, from the transgenic animal can be isolated and induced to exit the growth cycle and enter $G_0$ phase. The quiescent cell then can be fused, e.g., through the use of electrical pulses, to an enucleated oocyte from an animal of the same species from which the quiescent cell is isolated. The reconstructed oocyte then is cultured such that it develops to morula or blastocyte, and then is transferred to a pseudopregnant female foster animal. The offspring borne of the female foster animal will be a clone of the animal from that the cell, e.g., the somatic cell, is isolated.

Additional Uses and Methods of the Invention

The nucleic acid molecules, proteins, protein homologues, antibodies of the present invention, and fragments of such moieties, may be used in one or more of the following methods: a) screening assays; b) detection assays (e.g., chromosomal mapping, tissue typing, forensic biology); c) predictive medicine (e.g., diagnostic assays, prognostic assays, monitoring clinical trials and pharmacogenomics); and d) methods of treatment (e.g., therapeutic and prophylactic). The protein of the invention interacts with other cellular proteins, and thus can be used for (i) regulation of cellular proliferation; (ii) regulation of cellular differentiation; (iii) regulation of cell survival, and (iv) regulation of cell function. The isolated nucleic acid molecules of the invention can be used to express the protein of the invention (e.g., via a recombinant expression vector in a host cell in gene therapy applications), to detect mRNA of the invention (e.g., in a biological sample) or to detect a genetic lesion in a gene of the invention and to modulate activity of endogenous mRNA, DNA or protein. In addition, a protein of the invention can be used to screen drugs or compounds that modulate the protein activity or expression, as well as to treat disorders characterized by insufficient or excessive production of endogenous protein. Screening for the production of protein forms that have decreased or aberrant activity compared to wild type protein can also be performed with the present invention. In addition, an antibody of the invention can be used to detect and to isolate proteins and to modulate protein activity. The invention further pertains to novel agents identified by the above-described screening assays and uses thereof for treatments as described herein.

1. Detection and Screening Assays

Activation of a G protein receptor in the presence of endogenous ligand allows for G protein receptor complex formation, thereupon leading to the binding of GTP to the G protein. The GTPase domain of the G protein slowly hydrolyzes the GTP to GDP resulting, under normal conditions, in receptor deactivation. However, constitutively activated receptors continue to hydrolyze GDP to GTP.

A non-hydrolyzable substrate of G protein, [$^{35}$S]GTPγS, can be used to monitor enhanced binding to membranes which express constitutively activated receptors. Traynor and Nahorski reported that [$^{35}$S]GTPγS can be used to monitor G protein coupling to membranes in the absence and presence of ligand (Traynor et al., Mol Pharmacol (1995) 47(4):848-54). A preferred use of such an assay system is for initial screening of candidate compounds, since the system is generically applicable to all G protein-coupled receptors without regard to the particular G protein that binds to the receptor.

$G_s$ stimulates the enzyme adenylyl cyclase, while $G_i$ and $G_o$ inhibit that enzyme. As is well known in the art, adenylyl cyclase catalyzes the conversion of ATP to cAMP; thus, constitutively activated GPCRs that couple the $G_s$ protein are associated with increased cellular levels of cAMP. Alternatively, constitutively activated GCPRs that might couple the $G_i$ (or $G_o$) protein are associated with decreased cellular levels of cAMP. See "Indirect Mechanism of Synaptic Transmission", Chpt.8, from Neuron to Brain (3$^{rd}$ Ed.), Nichols et al. eds., Sinauer Associates, Inc., 1992. Thus, assays that detect cAMP can be used to determine if a candidate compound is an inverse agonist to the receptor. A variety of approaches known in the art for measuring cAMP can be utilized. In one embodiment, anti-cAMP antibodies are used in an ELISA-based format. In another embodiment, a whole cell second messenger reporter system assay is contemplated (see PCT Publication No. WO 00/22131 and incorporated by reference herein in their entireties). A particular embodiment is the SPA assay described below in "Example 5".

In a related aspect, cyclic AMP drives gene expression by promoting the binding of a cAMP-responsive DNA binding protein or transcription factor (CREB) which then binds to the promoter at specific sites called cAMP response elements, and drives the expression of the gene. Thus, reporter systems can be constructed which have a promoter containing multiple cAMP response elements before the reporter gene, e.g., β-galactosidase or luciferase. Further, as a constitutively activated $G_s$-linked receptor causes the accumulation of cAMP, that then activates the gene and expression of the reporter protein. The reporter protein, such as β-galactosidase or luciferase, then can be detected using standard biochemical assays (PCT Publication No. WO 00/22131 incorporated by reference herein).

Other G proteins, such as $G_o$ and $G_q$, are associated with activation of the enzyme, phospholipase C, which in turn hydrolyzes the phospholipid, PIP2, releasing two intracellular messengers: diacylglycerol (DAG) and inositol 1,4,5-triphosphate (IP3). Increased accumulation of IP3 is associated with activation of $G_q$-associated receptors and $G_o$-associated receptors (PCT Publication No. WO 00/22131 incorporated by reference herein). Assays that detect IP3 accumulation can be used to determine if a candidate compound is an inverse agonist to a $G_q$-associated receptor or a $G_o$-associated receptor. $G_q$-associated receptors also can be examined using an AP1 reporter assays that measures whether $G_q$-dependent phospholipase C causes activation of genes containing AP1 elements. Thus, activated $G_q$-associated receptors will demonstrate an increase in the expression of such genes, whereby inverse agonists will demonstrate a decrease in such expression.

Also provided herein is a method (also referred to herein as a "screening assay") for identifying modulators, i.e., candidate or test compounds or agents (e.g., peptides, peptidomimetics, small molecules or other drugs) that bind to proteins of the invention or have a stimulatory or inhibitory effect on, for example, expression or activity of the protein. For example, the screening assays described herein could be used to identify compounds acting as antagonists at the receptor that would have utility for treating bronchial asthma.

In one embodiment, the invention provides assays for screening candidate or test compounds that bind to or modulate the activity of the membrane-bound form of the protein of the invention, polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des (1997) 12:145).

Examples of methods for the synthesis of molecular libraries can be found in the art, for example in: DeWitt et al., Proc Natl Acad Sci USA (1993) 90:6909; Erb et al., Proc Natl Acad Sci USA (1994) 91:11422; Zuckermann et al., J Med Chem (1994) 37:2678; Cho et al., Science (1993) 261:1303; Carrell et al., Angew Chem Int Ed Engl (1994) 33:2059; Carell et al., Angew Chem Int Ed Engl (1994) 33:2061; and Gallop et al., J Med Chem (1994) 37:1233.

Libraries of compounds may be presented in solution (e.g., Houghten Bio/Techniques (1992) 13:412-421) or on beads (Lam, Nature (1991) 354:82-84), chips (Fodor, Nature (1993) 364:555-556), bacteria (U.S. Pat. No. 5,223,409), spores (U.S. Pat. Nos. 5,571,698; 5,403,484; and 5,223,409), plasmids (Cull et al., Proc Natl Acad Sci USA (1992) 89:1865-1869) or phage (Scott et al., Science (1990) 249:386-390; Devlin, Science (1990) 249:404-406; Cwirla et al., Proc Natl Acad Sci USA (1990) 87:6378-6382; and Felici, J Mol Biol (1991) 222:301-310); the disclosures of each of the foregoing references are incorporated herein by reference In a particular embodiment of the present invention, an assay is a cell-based assay in which a cell that expresses a membrane-bound form of the protein of the invention, or a biologically active portion thereof, on the cell surface is contacted with a test compound and the ability of the test compound to bind to the protein is determined. The cell, for example, can be a yeast cell or a cell of mammalian origin. Determining the ability of the test compound to bind to the protein can be accomplished, for example, by coupling the test compound with a radioisotope or enzymatic label so that binding of the test compound to the protein of the invention or biologically active portion thereof can be determined by detecting the labeled compound in a complex. For example, test compounds can be labeled with $^{125}I$, $^{35}S$, $^{14}C$ or $^{3}H$, either directly or indirectly and the radioisotope detected by direct counting of radioemmission or by scintillation counting. Alternatively, test compounds can be labeled enzymatically with, for example, horseradish peroxidase, alkaline phosphatase or luciferase and the enzymatic label detected by determination of conversion of an appropriate substrate to product. In a particular embodiment, the assay comprises contacting a cell that expresses a membrane-bound form of the protein of the invention or a biologically active portion thereof, on the cell surface with a known compound that binds the protein to form an assay mixture. Then, contacting the assay mixture with a test compound and determining the ability of the test compound to interact with the protein, wherein determining the ability of the test compound to interact with the protein comprises determining the ability of the test compound to bind preferentially to the protein of the invention or a biologically active portion thereof as compared to the known compound.

In another embodiment, an assay is a cell-based assay comprising contacting a cell expressing a membrane-bound form of the protein of the invention or a biologically active portion thereof, on the cell surface with a test compound and determining the ability of the test compound to modulate (e.g., stimulate or inhibit) the activity of the protein or biologically active portion thereof. Determining the ability of the test compound to modulate the activity of the protein of the invention or a biologically active portion thereof can be accomplished, for example, by determining the ability of the protein to bind to or to interact with a target molecule. As used herein, a "target molecule" is a molecule with which the protein of the invention binds or interacts with in nature, for example, a molecule on the surface of a cell that expresses the protein of the invention, a molecule on the surface of a second cell, a molecule in the extracellular milieu, a molecule associated with the internal surface of a cell membrane or a cytoplasmic molecule. A target molecule can be another molecule or a protein or polypeptide of the present invention. In one embodiment, a target molecule is a component of a signal transduction pathway that facilitates transduction of an extracellular signal (e.g., a signal generated by binding of a compound to a membrane-bound protein of the invention) through the cell membrane and into the cell. The target, for example, can be a second intercellular protein that has catalytic activity or a protein that facilitates the association of downstream signaling molecules.

Determining the ability of the protein of the instant application to interact with a target molecule can be accomplished by one of the methods described above for determining direct binding. In a particular embodiment, determining the ability of the protein of the invention to bind to or to interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3 etc.), detecting catalytic/enzymatic activity of the target on an appropriate substrate, detecting the induction of a reporter gene (e.g., a responsive regulatory element operably linked to a nucleic acid encoding a detectable marker, e.g. luciferase) or detecting a cellular response, e.g., cellular differentiation, proliferation or function. A particular embodiment is described below in "Example 4" where the receptor of the invention is coupled to Gα16 to elicit a calcium response.

The present invention further extends to a cell-free assay comprising contacting a protein of the invention, or biologically active portion thereof, with a test compound, and determining the ability of the test compound to bind to the protein or biologically active portion thereof. Binding of the test compound to the protein can be determined either directly or indirectly as described above. In a preferred embodiment, the assay includes contacting the protein of the invention or biologically active portion thereof with a known compound that binds the protein to form an assay mixture. Then, contacting the assay mixture with a test compound, and determining the ability of the test compound to interact with the protein. Wherein, determining the ability of the test compound to interact with the protein of the invention comprises determining the ability of the test compound to preferentially bind to the protein or biologically active portion thereof as compared to the known compound.

Another cell-free assay of the present invention involves contacting the protein of the invention or biologically active portion thereof, with a test compound and determining the ability of the test compound to modulate (e.g., stimulate or inhibit) the activity of the protein or biologically active portion thereof. Determining the ability of the test compound to modulate the activity of the protein can be accomplished, for example, by determining the ability of the protein to bind to a target molecule by one of the methods described above for determining direct binding. In an alternative embodiment, determining the ability of the test compound to modulate the activity of the protein can be accomplished by determining the ability of the protein to further modulate a target molecule. For example, the catalytic/enzymatic activity of the target molecule on an appropriate substrate can be determined as described previously.

Still another cell-free assay of the present invention comprises contacting the protein of the invention or biologically active portion thereof, with a known compound that binds the protein to form an assay mixture, contacting the assay mixture with a test compound and determining the ability of the test compound to interact with the protein. The step for determining the ability of the test compound to interact with the protein comprises determining the ability of the protein preferentially to bind to or to modulate the activity of a target molecule.

Receptors can be activated by non-ligand molecules that necessarily do not inhibit ligand binding but cause structural changes in the receptor to enable G protein binding or, perhaps receptor aggregation, dimerization or clustering that can cause activation. For example, antibodies can be raised to the various portions of the receptor of the invention that are exposed at the cell surface. Those antibodies activate a cell via the G protein cascade as determined by standard assays, such as monitoring cAMP levels or intracellular $Ca^{+2}$ levels. Because molecular mapping, and particularly epitope mapping, is involved, monoclonal antibodies may be preferred.

The monoclonal antibodies can be raised both to intact receptor expressed at the cell surface and peptides known to form at the cell surface. The method of Geysen et al., U.S. Pat. No. 5,998,577, can be practiced to obtain a plurality of relevant peptides.

Antibodies found to activate the receptor of the invention may be modified to minimize activities extraneous to receptor activation, such as complement fixation. Thus, the antibody molecules can be truncated or mutated to minimize or to remove activities outside of receptor activation. For example, for certain antibodies, only the antigen-binding portion is needed. Thus, the $F_c$ portion of the antibody can be removed.

Cells expressing the receptor of the invention are exposed to antibody to activate the receptor. Activated cells then are exposed to various molecules in order to identify which molecules modulate receptor activity, and result in higher activation levels or lower activation levels. Molecules that achieve those goals then can be tested on cells expressing the receptor of the invention without antibody to observe the effect on non-activated cells. The target molecules then can be tested and modified as candidate drugs for the treatment of disorders associated with altered metabolism using known techniques.

The cell-free assays of the present invention are amenable to use of both the soluble form and the membrane-bound form of the protein of the invention. In the case of cell-free assays comprising the membrane-bound form, it may be desirable to utilize a solubilizing agent such that the membrane-bound form is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON X-100, TRITON X-114, THESIT, isotridecylpoly(ethylene glycol ether)$_n$, 3-[(3-cholamidopropyl)dimethylamino]-1-propane sulfonate (CHAPS), 3-[(3-cholamidopropyl)dimethylamino]-2-hydroxy-1-propane sulfonate (CHAPSO) or N-dodecyl-N,N-dimethyl-3-ammonio-1-propane sulfonate.

In more than one embodiment of the above assay methods of the present invention, it may be desirable to immobilize either the protein of the invention or a target molecule thereof to facilitate separation of complexed from uncomplexed forms of one or both of the proteins, as well as to accommodate automation of the assay. Binding of a test compound to the protein of the invention or interaction of the protein with a target molecule in the presence and absence of a candidate compound, can be accomplished in any vessel suitable for containing the reactants. Examples of such vessels include microtitre plates, test tubes and micro-centrifuge tubes. In one embodiment, a fusion protein can be provided that adds a domain that allows one or both of the proteins to be bound to a matrix. For example, glutathione-S-transferase/protein of the invention fusion proteins or glutathione-S-transferase/target fusion proteins can be adsorbed onto glutathione SEPHAROSE beads (Sigma Chemical, St. Louis, Mo.). Alternatively, glutathione-derivatized microtitre plates are then combined with the test compound. Subsequently, either the non-adsorbed target protein or the protein of the invention and the mixture are incubated under conditions conducive to complex formation (e.g., at physiological conditions for salt and pH). Following incubation, the beads or microtitre plate wells are washed to remove any unbound components, and the presence of complex formation is measured either directly or indirectly. Alternatively, the complexes can be dissociated from the matrix and the level of binding or activity determined using standard techniques.

Other techniques for immobilizing proteins on matrices can also be used in the screening assays of the invention. For example, either the protein of the invention or a target molecule thereof can be immobilized utilizing conjugation of biotin and streptavidin. Biotinylated protein of the invention or target molecules can be prepared from biotin-NHS (N-hydroxy-succinimide) using techniques well known in the art (e.g., biotinylation kit, Pierce Chemicals, Rockford, Ill.) and immobilized in the wells of streptavidin-coated 96-well plates (Pierce Chemicals). Alternatively, antibodies that are reactive with proteins of the invention or a target molecule, but do not interfere with binding of the protein of the invention to the target molecule, can be derivatized to the wells of the plate. Upon incubation, unbound target or protein of the invention can be trapped in the wells by antibody conjugation. Methods for detecting such complexes, in addition to those described above for the GST-immobilized complexes, include immunodetection of complexes using antibodies reactive with proteins of the invention or target molecule, as well as enzyme-linked assays that rely on detecting an enzymatic activity associated with the protein of the invention or target molecule.

In another embodiment, modulators of protein expression are identified in a method wherein a cell is contacted with a candidate compound, and the expression of mRNA or protein of the invention in the cell is determined. The level of expression of mRNA or protein in the presence of the candidate compound is compared to the level of expression of mRNA or protein in the absence of the candidate compound. The candidate compound then can be identified as a modulator of expression based on that comparison. For example, when expression of mRNA or protein is greater (statistically significantly greater) in the presence of the candidate compound than in the absence thereof, the candidate compound is identified as a stimulator or agonist of mRNA or protein expression. Alternatively, when expression of mRNA or protein is less (statistically significantly less) in the presence of the candidate compound than in the absence thereof, the candidate compound is identified as an inhibitor or antagonist of mRNA or protein expression. If activity is reduced in the presence of ligand or agonist, or in a constitutively expressing cell is below baseline, the candidate compound is identified as an inverse agonist. The level of mRNA or protein expression in the cells can be determined by methods described herein for detecting mRNA or protein.

In yet another aspect of the invention, the proteins of the invention can be used as "bait proteins" in a two-hybrid assay or three-hybrid assay (see, e.g., U.S. Pat. No. 5,283,317; Zervos et al., Cell (1993) 72:223-232; Madura et al., J Biol Chem (1993) 268:12046-12054; Bartel et al., Bio/Techniques (1993) 14:920-924; Iwabuchi et al., Oncogene (1993) 8:1693-1696; and PCT Publication No. WO 94/10300, the disclosures of each of which are incorporated herein by reference), to identify other proteins that bind to or interact with the protein of the invention and modulate the activity of the protein of the invention. Such binding proteins are also likely to be involved in the propagation of signals by the proteins of the invention such as, upstream or downstream elements of the signaling pathway.

Since the present invention enables the production of large quantities of pure protein of the instant application, physical characterization of the conformation of areas of likely function can be ascertained for rational drug design. For example, the intracellular and extracellular domains are regions of particular interest. Once the shape and ionic configuration of a region is discerned, candidate drugs that should interact with those regions can be configured and then tested in intact cells, animals and patients. Methods that would enable deriving such 3-D structure information include X-ray crystallography, NMR spectroscopy, molecular modeling and so on. The 3-D structure also can lead to identification of analogous conformational sites in other known proteins where known drugs that interact at this site exist. These drugs, or derivatives thereof, may find use with protein of the present invention.

The screening assays described above would be of particular utility in identifying compounds acting as an agonist, partial agonist, antagonist, inverse agonist or modulator of the receptor of the invention providing a means to identify compounds for the treatment of disease including, but not limited to, bronchial asthma, COPD, allergic rhinitis, allergic dermatitis, allergic conjuctivitis, systemic mastocytosis and ischemic reperfusion injury.

The invention further pertains to novel agents identified by the above-described screening assays and uses thereof for treatments as described herein.

Portions or fragments of the DNA sequences of the present invention can be used in numerous ways as polynucleotide reagents. For example, the sequences can be used to: (i) map the respective genes on a chromosome and, thus, locate gene regions associated with genetic disease; (ii) identify an individual from a minute biological sample (tissue typing); and (iii) aid in forensic identification of a biological sample. The applications are described in the subsections below.

2. Chromosome Mapping

Once the sequence (or a portion of the sequence) of a gene has been isolated, the sequence can be used to map the location of the gene of the present invention on a chromosome. Accordingly, nucleic acid molecules described herein or fragments thereof can been used to map the location in a genome. The mapping of the location of the sequence in a genome, particularly a human genome, is an important first step in correlating the sequences with genes associated with disease.

Briefly, genes can be mapped in a genome by preparing PCR primers (preferably 15-25 bp in length) from the sequences disclosed in SEQ ID NO:1. The primers are used for PCR screening of somatic cell hybrids containing individual human chromosomes. Only those hybrids containing the human gene corresponding to sequences of the invention yield an amplified fragment.

Somatic cell hybrids are prepared by fusing somatic cells from different mammals (e.g., human and mouse cells). As hybrids of human and mouse cells grow and divide, generally human chromosomes are lost in random order, but the mouse chromosomes are retained. By using media in which mouse cells cannot grow (because of lack of a particular enzyme), but in which human cells can grow, the one human chromosome that contains the gene encoding the needed enzyme will be retained. By using various media, panels of hybrid cell lines are established. Each cell line in a panel contains either a single human chromosome or a small number of human chromosomes and a full set of mouse chromosomes, allowing easy mapping of individual genes to specific human chromosomes. (D'Eustachio et al., Science (1983) 220:919-924). Somatic cell hybrids containing only fragments of human chromosomes also can be produced by using human chromosomes with translocations and deletions.

PCR mapping of somatic cell hybrids is a rapid procedure for assigning a particular sequence to a particular chromosome. Three or more sequences can be assigned per day using a single thermocycler.

Other mapping strategies that can similarly be used to map a sequence to a particular chromosome in a genome include in situ hybridization (described in Fan et al., Proc Natl Acad Sci USA (1990) 87:6223-27), pre-screening with labeled flow-sorted chromosomes and pre-selection by hybridization to chromosome-specific cDNA libraries.

Fluorescence in situ hybridization (FISH) of a DNA sequence to a metaphase chromosomal spread can also be used to provide a precise chromosomal location in one step. Chromosome spreads can be made using cells in which division has been blocked in metaphase by a chemical, e.g., colcemid, that disrupts the mitotic spindle. The chromosomes can be treated briefly with trypsin and then stained with Giemsa. A pattern of light and dark bands develops on each chromosome so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases and more preferably, 2,000 bases will suffice to get good results in a reasonable amount of time. For a review of the technique, see Verma et al. (Human Chromosomes: A Manual of Basic Techniques (Pergamon Press, New York, 1988)). Chromosomal mapping can be inferred in silico, and employing statistical considerations, such as lod scores or mere proximity.

Reagents for chromosome mapping can be used individually to locate a single site on a chromosome. Furthermore, panels of reagents can be used for marking multiple sites and/or multiple chromosomes. Reagents corresponding to flanking regions of the gene actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data. (Such data are found, for example, in McKusick, Mendelian Inheritance in Man, available on-line through Johns Hopkins University, Welch Medical Library). The relationship between genes and disease, mapped to the same chromosomal region, can then be identified through linkage analysis (co-inheritance of physically adjacent genes), described in, e.g., Egeland et al., Nature (1987) 325:783-787.

Moreover, differences in the DNA sequences between individuals affected and unaffected with a disease associated with the protein of the invention can be determined. If a mutation is observed in some or all of the affected individuals, but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

3. Diagnostic Assays

An exemplary method for detecting the presence or absence of a nucleic acid or protein of the invention in a biological sample involves obtaining a biological sample from a test subject and contacting the biological sample with a compound or an agent capable of detecting the protein or nucleic acid (e.g., mRNA or genomic DNA) such that the presence is detected in the biological sample. A preferred agent for detecting mRNA or genomic DNA is a labeled nucleic acid probe capable of hybridizing to the mRNA or genomic DNA of the invention. The nucleic acid probe can be, for example, a full-length nucleic acid, such as the nucleic acid of SEQ ID NO:1 or a portion thereof, such as an oligonucleotide of at least 15, 30, 50, 100, 250 or 500 or more nucleotides in length and sufficient to specifically hybridize under stringent conditions to mRNA or genomic DNA. Other suitable probes for use in the diagnostic assays of the invention are described herein.

A particular agent for detecting the protein of the invention is an antibody capable of binding to the protein, preferably an antibody with a detectable label. Antibodies can be polyclonal, chimeric, or more preferably, monoclonal. An intact antibody or a fragment thereof (e.g., $F_{ab}$ or $F_{(ab')2}$) can be used. The term "biological sample" is intended to include tissues, cells and biological fluids isolated from a subject, as well as tissues, cells and fluids present within a subject. That is, the detection method of the invention can be used to detect mRNA, protein or genomic DNA in a biological sample in vitro as well as in vivo. For example, in vitro techniques for detection of mRNA include Northern hybridization and in situ hybridization. In vitro techniques for detection of the protein include ELISA, Western blot, immunoprecipitation and immunofluorescence. In vitro techniques for detection of genomic DNA include Southern hybridization. Furthermore, in vivo techniques for detection of protein include introducing into a subject a labeled antibody against the protein of the invention. For example, the antibody can be labeled with a radioactive marker, the presence and location of which in a subject can be detected by standard imaging techniques.

In an embodiment, the biological sample contains protein molecules from the test subject. Alternatively, the biological sample can contain mRNA molecules from the test subject or genomic DNA molecules from the test subject. A particular biological sample having applications herein is a neutrophil sample isolated by conventional means from a subject.

Hence, association with a disease and identification of nucleic acid or protein polymorphism diagnostic for the carrier or the affected can be beneficial in developing prognostic or diagnostic assays. For example, it would be beneficial to have a prognostic or diagnostic assay for rheumatoid arthritis, asthma, Crohn's Disease and so on. Expression of the nucleic acid or protein of the invention is elevated in cells associated with activated or inflammatory states. Disorders associated with inflammation include, anaphylactic states, colitis, Crohn's Disease, edematous states, contact hypersensitivity, allergy, other forms of arthritis, meningitis and other conditions wherein the immune system reacts to an insult by vascular dilation, heat, collecting cells, fluids and the like at a site resulting in swelling and the like. Thus, a disorder in metabolism may be diagnostic for rheumatoid arthritis. Moreover, the molecular mechanism of rheumatoid arthritis may be detectable, such as, there may be a diagnostic SNP, RFLP, variability of expression level, variability of function and so on, that can be detectable in a tissue sample, such as a blood sample.

In another embodiment, the methods further involve obtaining a biological sample from a control subject, contacting the control sample with a compound or agent capable of detecting protein, mRNA or genomic DNA of the invention, such that the presence and amount of protein, mRNA or genomic DNA is detected in the biological sample, and then comparing the presence and amount of protein, mRNA or genomic DNA in the control sample with the presence and amount of protein, mRNA or genomic DNA in a test sample.

4. High Throughput Assays of Chemical Libraries

Any of the assays for compounds capable of modulating the activity of nucleic acid or protein of the invention are amenable to high throughput screening. High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols of the various high throughput protocols. Thus, for example, Zymark Corp. provides technical bulletins describing screening systems for detecting the modulation of gene transcription, ligand binding, and the like.

5. Kits

The invention also encompasses kits for detecting the presence of the nucleic acid or protein of the invention in a biological sample (a test sample). Such kits can be used to determine if a subject is suffering from or is at increased risk of developing a disorder associated with aberrant expression (e.g., an immunological disorder). For example, the kit can comprise a labeled compound or agent capable of detecting protein or mRNA of the invention in a biological sample and means for determining the amount of nucleic acid or protein in the sample (e.g., an antibody or an oligonucleotide probe). Kits also can be used to yield results indicating whether the tested subject is suffering from or is at risk of developing a disorder associated with aberrant expression of nucleic acid or protein of the invention, if the amount of protein or mRNA is above or below a normal level.

For antibody-based kits, the kit can comprise, for example: (1) a first antibody (e.g., attached to a solid support) that binds to the protein of the invention; and, optionally, (2) a second, different antibody that binds to the protein of the invention or to the first antibody and is conjugated to a detectable agent. If the second antibody is not present, then either the first antibody can be detectably labeled, or alternatively, another molecule that binds the first antibody can be detectably labeled. In any event, a labeled binding moiety is included to serve as the detectable reporter molecule, as known in the art.

For oligonucleotide-based kits, a kit of the present invention can comprise, for example: (1) an oligonucleotide, e.g., a detectably-labeled oligonucleotide, that hybridizes to a nucleic acid sequence of the invention or (2) a pair of primers useful for amplifying a nucleic acid molecule of the invention.

The kit also can comprise, e.g., a buffering agent, a preservative or a protein stabilizing agent. The kit also can comprise components necessary for detecting the detectable agent (e.g., an enzyme or a substrate). Furthermore, the kit may also contain a control sample or series of control samples that can be assayed and compared to the test sample. Each component of the kit is usually enclosed within an individual container, and all of the various containers are within a single package. Instructions and background information may also be enclosed.

6. Monitoring of Effects During Clinical Trials

Monitoring the influence of agents (e.g., drugs or compounds) on the expression or activity of the nucleic acids or proteins of the invention (e.g., the ability to modulate aberrant cell proliferation, differentiation and/or function) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels or protein activity. Alternatively, the effectiveness of an agent, as determined by a screening assay, to decrease gene expression, protein levels or protein activity, can be monitored in clinical trials of subjects exhibiting increased gene expression, protein levels or protein activity. In such clinical trials, expression or activity and preferably, that of other genes that have been implicated in, for example, a cellular proliferation disorder, can be used as a marker of the immune responsiveness of a particular cell. For example, and not by way of limitation, genes, including the genes of the invention, that are modulated in cells by treatment with an agent (e.g., compound, drug or small molecule) that modulates activity of the nucleic acid or protein of the invention (e.g., as identified in a screening assay described herein) can be identified. Thus, to study the effect of agents on cellular proliferation disorders, for example, in a clinical trial, cells can be isolated and RNA prepared and analyzed for the levels of expression of nucleic acids of the invention and other genes implicated in the disorder. The levels of gene expression (i.e., a gene expression pattern) can be quantified by Northern blot analysis or RT-PCR, as described herein, or alternatively by measuring the amount of protein produced by one of the methods as described herein or by measuring the levels of activity of genes of the invention or other genes. In that way, the gene expression pattern can serve as a marker, indicative of the physiological response of the cells to the agent. Accordingly, the response state may be determined before and at various points during treatment of the individual with the agent.

In a particular embodiment, the present invention provides a method for monitoring the effectiveness of treatment of a subject with an agent (e.g., an agonist, antagonist, peptidomimetic, protein, peptide, nucleic acid, small molecule or other drug candidate identified by the screening assays described herein) comprising the steps of (i) obtaining a pre-administration sample from a subject prior to administration of the agent; (ii) detecting the level of expression of a protein, mRNA or genomic DNA of the invention in the preadministration sample; (iii) obtaining one or more post-administration samples from the subject; (iv) detecting the level of expression or activity of the protein, mRNA or genomic DNA of the invention in the post-administration samples; (v) comparing the level of expression or activity of the protein, mRNA or genomic DNA of the invention in the pre-administration sample with the protein, mRNA or genomic DNA in the post-administration sample or samples; and (vi) altering the administration of the agent to the subject accordingly. For example, increased administration of the agent may be desirable to increase the expression or activity of the protein, mRNA or genomic DNA of the invention to higher levels than detected, i.e., to increase the effectiveness of the agent. Alternatively, decreased administration of the agent may be desirable to decrease expression or activity of the protein, mRNA or genomic DNA of the invention to lower levels than detected, i.e., to decrease the effectiveness of the agent.

The following examples describe the invention in greater detail.

EXAMPLES

Example 1

Cloning of an Initial Exonic DNA Fragment of the Guinea Pig DP Receptor

Cloning of the *Cavia porcellus* DP receptor cDNA was initiated by cloning an exonic fragment of the DP receptor from genomic DNA using PCR. A range of PCR primers were designed using the conserved regions of the Human (U31332), Mouse (NM_008962) and Rat (NM_022241) DP receptor sequences that aligned using the program Sequencher (Gene Codes, Ann Arbor Mich.). *Cavia porcellus* (guinea pig) genomic DNA was purchased from CeMines (Evergreen, Co.). The primer used to amplify a 420 bp fragment of *Cavia* genomic DNA was performed with the primers 675_Topo_F3 (SEQ ID NO: 3: GGGACACCCTTTCTTC-TACAA) and 675_Topo_R2 (SEQ ID NO: 4: GAACA-CATGGTGAAGAGCACTG). The PCR product was cloned using TOPO-TA cloning (Invitrogen, Carlsbad Calif.) and the insert was sequenced on an ABI 3100 DNA sequencer according to the manufacturer's instructions.

3' and 5' RACE-PCR Cloning

The resulting DNA sequence was aligned to the human, mouse and rat DP sequences. The alignment revealed that the PCR product sequence was homologous to, but yet distinct from, the DP receptor consensus from the species examined (FIG. 3). The *Cavia porcellus* DP receptor consensus was used to design additional primers to extend the cloned sequence using the rapid amplification of DNA ends (RACE) method. In order to obtain 3' end of the DP receptor transcript, the SMART RACE system from Clontech (a subsidiary of BD Biosciences, Palo Alto Calif.) was employed. The primer 675_GP_3'RACE_F (SEQ ID NO: 5: GTGCTCGTG-GCGCCGGTGTG) was used with *Cavia* lung mRNA converted to a cDNA template to extend the *Cavia* DP receptor mRNA sequence. RACE products were cloned into PCR4-Topo (Invitrogen, Carlsbad Calif.), sequenced and aligned as described above to reveal complete 3' extension of the coding sequence of the DP receptor. In order to isolate the 5' end of the *Cavia* DP receptor cDNA, SMART RACE was performed with the primer 675_Rev_P2 (SEQ ID NO: 6: CACATGGT-GAAGAGCACGGTCATGA) and a 1 kb PCR product was generated. The purified PCR product was used as a template for 5' Nested RACE using the primer 675_RACE_R9 (SEQ ID NO: 7: TCACCAGGCACTTGCCTAGCAGGTCTGT). The RACE products were cloned into PCR4-Topo (Invitrogen), sequenced and aligned as described above to reveal complete 5' extension of the coding sequence of the DP receptor.

Construction of cDNA Encoding the Guinea Pig DP Receptor

The coding sequence of the DP receptor was identified using the program Gene Construction Kit (Textco, Keene N.H.). Gateway cloning compatible primers were designed to flank the coding sequence (GW675, forward primer SEQ ID NO: 8: AAAAGCAGGCTTAGGAATGTCCTTC-TATCCCTGCAACAC; GW675, reverse primer SEQ ID NO: 9 AAGAAAGCTGGGTCTCACAGACTGGAT-TCCACGTTAG), and utilized in a PCR reaction with cDNA generated from the *Cavia porcellus* ovalbumin-stimulated lung cells. PCR was performed using 10 units of PFU Turbo (Stratagene, La Jolla Calif.) thermostable polymerase and 100 ng of template cDNA. A 1.1 kb DNA fragment was generated, purified by gel electrophoresis chromatography by the QiaQuick protocol (Qiagen) and cloned into the pDONR201 vector using the Gateway BP recombinase cloning method (Invitrogen). Cloning reactions were transformed into *E. coli* DH5-alpha and mini-prep DNA from the resultant colonies were subjected to DNA sequencing to confirm cloning of the complete DP receptor coding sequence.

Example 2

Northern Blot Analysis

Figure 5:
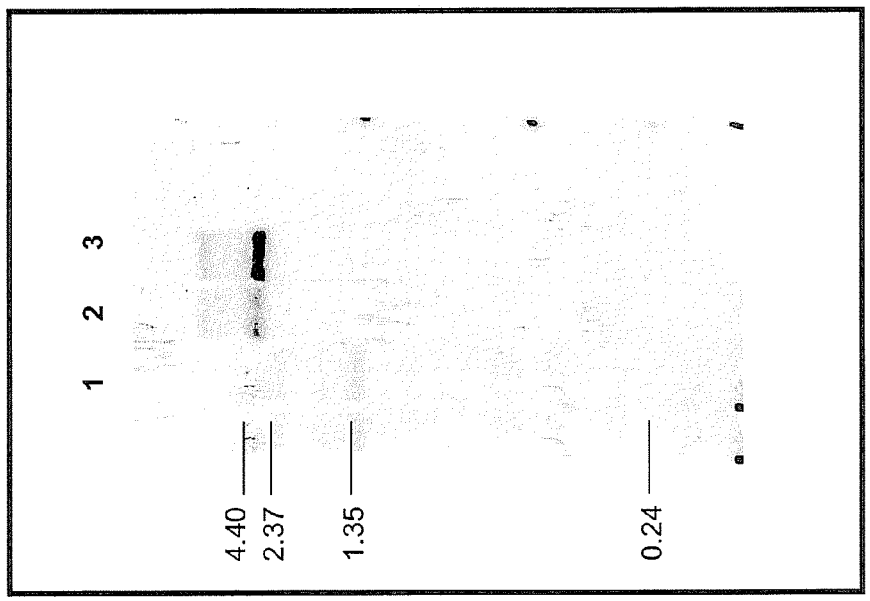
FIG. 5 shows a Northern blot analysis of genomic DNA fragment of the *Cavia porcellus* DP receptor. Lane 1: Invitrogen 0.24-9.5 Kb RNA ladder; Lane 2: Total lung RNA from *Cavia porcellus* unchallenged; Lane 3: Total lung RNA from *Cavia porcellus* ovalbumin challenged.

Northern blot analysis was performed with the initial genomic DNA fragment of the *Cavia* DP receptor (FIG. 5). Lung was isolated from male Hartley Guinea pigs that had been and challenged with ovalbumin or had not received ovalbumin treatment. Total lung RNA expression from unchallenged *Cavia porcellus* (Lane 2) was compared to total lung RNA expression from ovalbumin challenged *Cavia porcellus* (Lane 3). RNA loaded was equivalent as determined by spectroscopy and intensity of the 18S RNA band. Northern blotting for the DP receptor identified a 3-4 kb mRNA in the guinea pig lung, a size consistent with the transcript reported for mouse and human DP (Hirata et al., 1994; Boie et al., 1995). This mRNA was significantly upregulated in the lungs of guinea pigs that had been sensitized and challenged with ovalbumin a result comparable with that reported previously for DP receptor being upregulated in the mouse lung on antigen challenge (Matsuoka et al., 2000). These data support the importance of DP in the asthmatic response in the guinea pig lung.

Example 3

Sequence Analysis of Guinea Pig to Orthologue DP Receptors

The nucleotide sequence (FIG. 1) and deduced amino acid sequence (FIG. 2) for the guinea pig DP receptor is shown. The guinea pig DP cDNA contains a 1,032 bp open reading frame which encodes a 345 amino acid protein with a calculated molecular mass of 38,250.

The guinea pig DP protein contains two potential N-glycosylation sites, Asn-7 in the amino terminus and Asn-86 in the first extracellular loop. There are also 2 potential protein kinase C phosphorylation sites, Ser-46 and Thr-140 located in the first and third cytoplasmic loops, respectively.

The nucleotide sequence of the guinea pig DP receptor compared with the corresponding sequences of human, rat and mouse DP are shown in FIG. 1. Similarly at the protein level, the sequence identity against the guinea pig DP receptor was 66% for human DP, 63% for mouse DP and 65% for rat DP (FIG. 2).

Hydropathy analysis confirmed the presence of seven putative transmembrane domains which mapped identically to conserved areas that had previously been defined in the sequences of mouse, rat and human DP. Sequence conservation was the highest in the transmembrane domains between the DP orthologues. Two sequence stretches that had previously been reported to be characteristically conserved amongst GPCRs of the prostanoid family (Hirata et al., 1994) were also present in the guinea pig DP protein: QYCPGTWCR (SEQ ID NO: 10) in the second extracellular loop and RFLSVISIVDPWIFI (SEQ ID NO: 11) in the seventh transmembrane domain were identical among all DP orthologues.

The extracellular loop between TMDs VI and VII also showed differences between species. This loop varied between the orthologues and had lengths of 24, 21, 21 and 18 amino acids in human, rat, mouse and guinea pig DP, respectively. Of particular note is the loss of 6 amino acids in guinea pig DP between TMDs VI and VII compared to the human DP receptor. Furthermore, 3 amino acids are also removed in this region in both the mouse and rat DP receptors. Kobayashi et al (2000) generated a series of chimeric IP-DP receptors to define the regions that confer the ligand binding selectivity of DP. It is interesting to note that one of the regions they concluded to be important in selective and potent binding of PGD2 was the transmembrane VI-VII region, the exact same region shown to be 6 amino acids shorter in this newly cloned guinea pig DP receptor. Orthologue differences in ligand affinity or compound potency may be due to interactions within the TMD VI-VII loop and the alterations in this loop on the guinea pig receptor.

The first and third intracellular loops are 3 and 5 amino acids shorter in the guinea pig DP protein, whereas in the mouse, human and rat DP proteins these intracellular loops are all of identical size. Kobayashi et al. also highlighted the importance of the transmembrane domain 1 to the first extracellular loop region for PGD2 binding. Since the first intracellular loop is 3 amino acids shorter in guinea pig DP compared to human, mouse or rat DP, this region could be an additional region contributing to receptor binding affinity. Additionally, this region of the receptor could attribute to the differences observed between the affinities of compounds to human and guinea pig DP. The third intracellular loop (between TMDs V and VI) is 5 amino acids shorter in guinea pig DP, providing another region on the receptor contributing to functional relevance of PGD2.

Example 4

Construction of pEAK10-gpDP and pEAK10-mDP Mammalian Expression Vectors

A full length cDNA for the mouse DP receptor was obtained by PCR and cloned into the pDONR201 vector using the Gateway BP recombinase cloning method. This generated a mouse DP vector that was analogous to the guinea pig DP vector described above. DNA sequencing confirmed that this mouse DP cDNA was identical to the previously described mouse DP sequence defined by Genbank accession number NM_008962. For expression studies, the mouse and guinea pig DP receptors were subcloned by an LR reaction into a pEAK10 expression vector (Edge Biosystems) that had been previously gateway adapted. Gateway adaptation of the pEAK10 vector was conducted by digesting with EcoRI and subsequent Klenow filling for cloning of the Gateway cassette into the vector. The resultant vectors pEAK10-gpDP and pEAK10-mDP were used for generation of stable cell lines as described below.

Generation of a HEK293-Gα16 Cell Line

The cDNA encoding human Gα16 was cloned as described (Amatruda et al., 1991). Briefly, total RNA from HL-60 human promyelocytic leukemia cells was isolated and used as a template for PCR-mediated synthesis of cDNA encoding Gα16. The resulting PCR product was cloned into the expression vector pHook-3 (Invitrogen), which also coexpresses a single-chain antibody (sFv) to allow convenient enrichment of transfected cells using a panning protocol with hapten-coated magnetobeads (Chesnut et al., 1996). HEK293 cells were transfected with the constructed plasmid (pGα16), selected with Zeocin and positive clones enriched using magnetobeads according to protocols supplied by the vendor. For final purification and selection, single clones were grown individually and assayed for functional expression of Gα16 by additional transfection of an aliquot with an expression vector for an arbitrarily chosen GPCR naturally coupling to Gαs (GIP receptor), with subsequent testing of transfected cells for calcium signalling using the FLIPR device from Molecular Devices Corp.

Expression of pEAK10-gpDP and pEAK10-mDP in HEK293-Gα16 Cells.

The pEAK10-gpDP and pEAK10-mDP vectors were transfected into the HEK293-Gα16 cell line using Lipofectamine 2000 (Gibco) as described by the manufacturer. Transfected cells were cultured under selection with 1 ug/ml puromycin and 250 ug/ml zeocin for 5 weeks. Expression of the DP receptor was monitored in the transfected cell population by measuring the release of intracellular calcium in response to PGD2 stimulation.

Intracellular Calcium Assays

Figure 6:
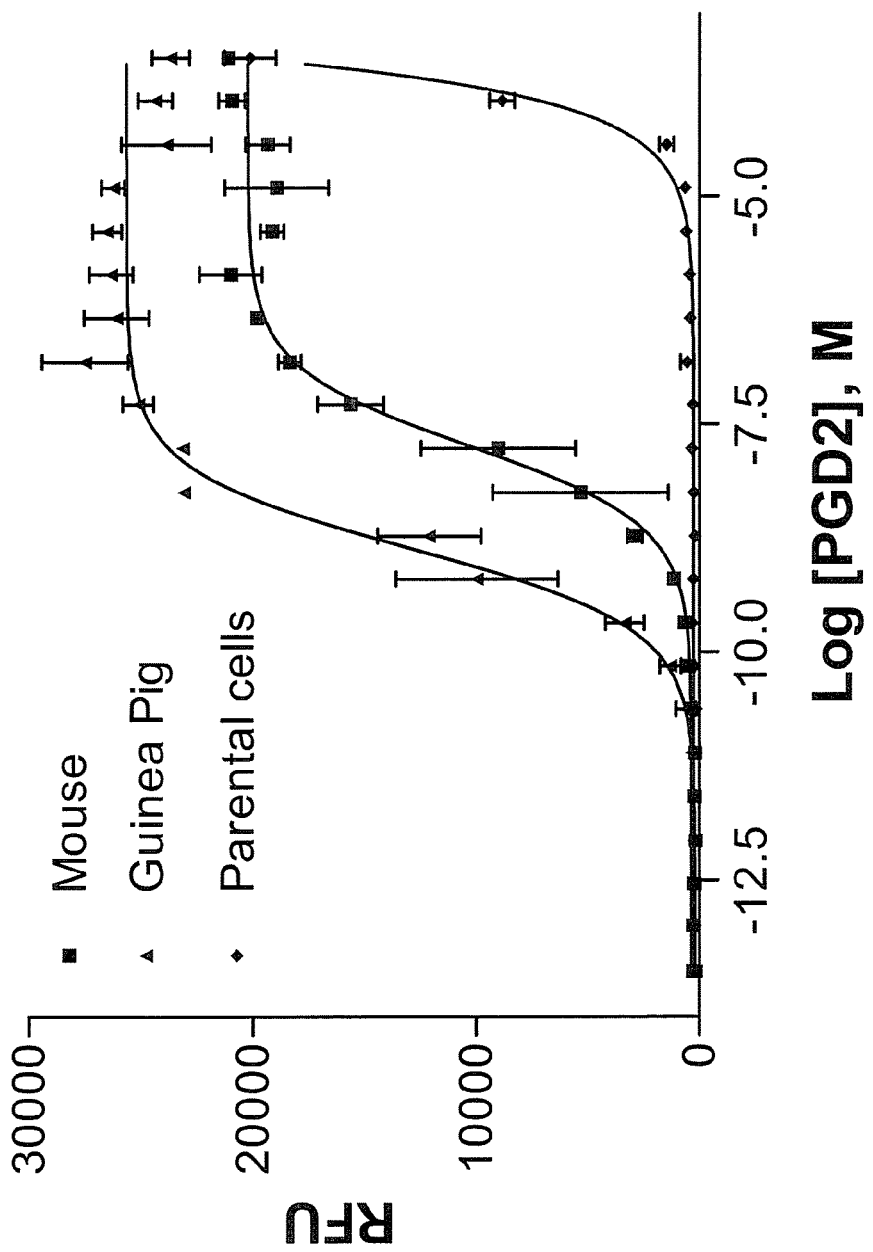
FIG. 6 shows an example of PGD2-induced calcium mobilization of recombinant guinea pig DP receptor (SEQ ID NO: 2) expressed in HEK-293-Gα16 cells stably transfected with SEQ ID NO: 1 compared to an equivalent cell line generated with the mouse DP receptor and the parental cell line.

For functional characterization the newly cloned guinea pig DP receptor was stably transfected into HEK293-Gα16 cells and for comparison an equivalent cell line was generated with the mouse DP receptor. Both DP receptor-expressing cell lines, as well as the parental cell line not expressing any transfected DP receptor, were evaluated in a second messenger assay using the force coupling of the receptor to Gα16 to elicit a calcium response. Intracellular calcium measurements were performed using non-transfected HEK293-Gα16 cells or cells transfected with either the pEAK10-gpDP or the pEAK10-mDP expression vectors. Transfected and non-transfected cells were plated in 384 well plates at 10,000 cells per well. Cells were washed three times with calcium assay buffer. Cells were then incubated with 4 µM of the calcium loading dye Fura-4/AM (Molecular Probes) at 37° C. for x min. Unincorporated fura-4/AM was removed by three further washes with calcium assay buffer. Intracellular calcium was measured following PGD2 or buffer stimulation of Fura-4/AM loaded cells using a FLIPR instrument (Molecular Devices Corp.). As shown in FIG. 6, PGD2 stimulation caused robust increases in intracellular calcium mobilization in both the guinea pig and mouse DP-expressing cell lines with EC50 values of 1.4 nM and 18 nM, respectively. The maximum calcium release in both cell lines was comparable. In contrast the parental HEK293-Gα16 cell line only showed a calcium response at very high PGD2 concentrations (i.e., above 10 µM PGD2).

Example 5

SPA cAMP Assay

Figure 7:
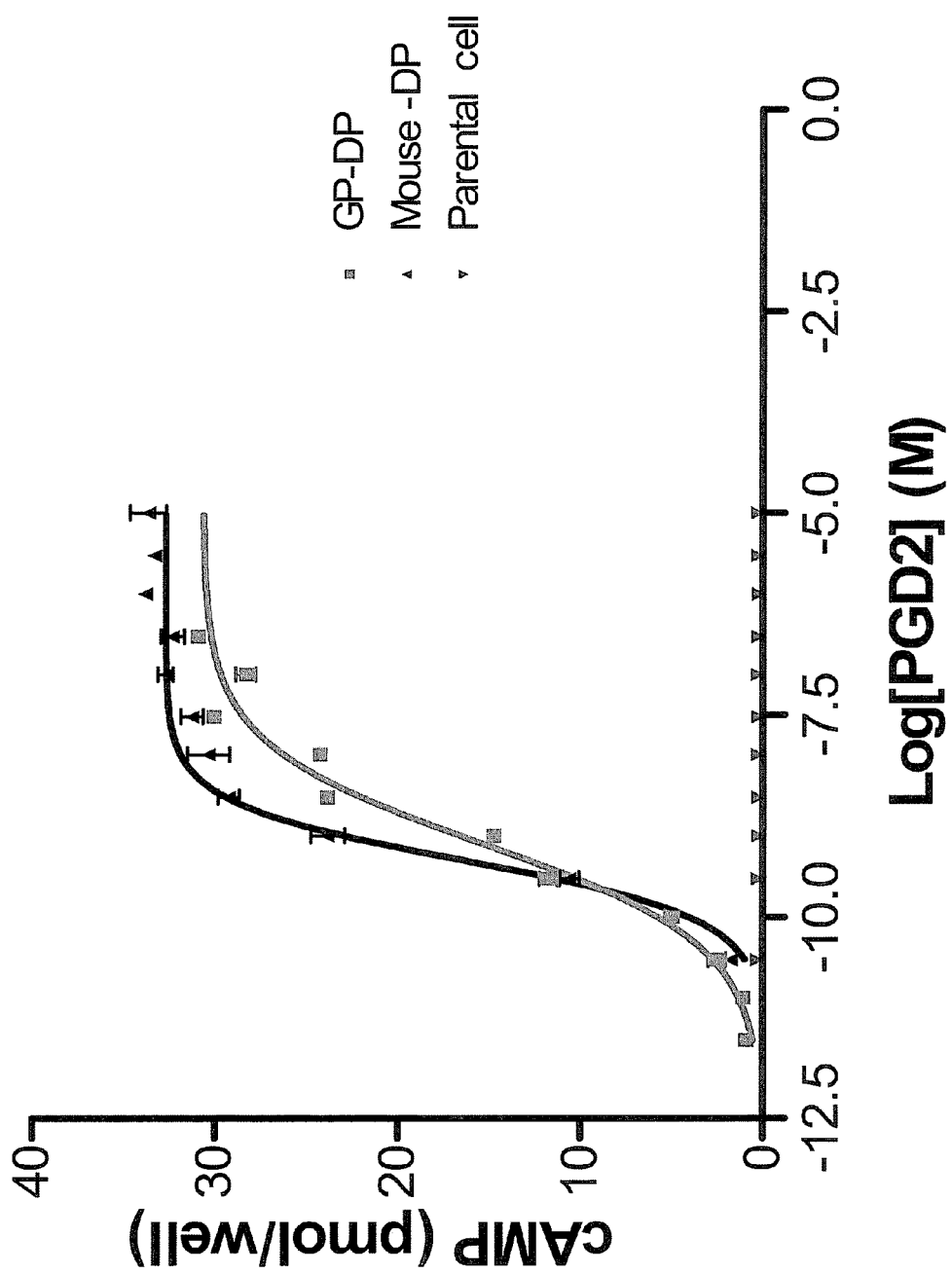
FIG. 7 shows an example PGD2 dose response curve of recombinant guinea pig DP receptor (SEQ ID NO: 2) expressed in HEK-293-Ga16 cells stably transfected with SEQ ID NO: 1 using the SPA cAMP assay. Comparison to an equivalent cell line generated with the mouse DP receptor and the parental cell line are included.

An additional functional characterization of the newly cloned guinea pig DP receptor used the natural signaling pathway for DP, the stimulation of cAMP production by adenylate cyclase. Transfected or non-transfected cells were plated at 40,000 cells per well of a 96 well plate. After overnight incubation at 37° C., medium was replaced and cells were stimulated with defined concentrations of PGD2 for 15 minutes. The accumulation of cAMP was measured in the stimulated cells using the cAMP SPA Direct Screening Assay System (Amersham) according to procedures specified by the manufacturer. As shown in FIG. 7, the guinea pig DP cell line exhibited a good cAMP response to PGD2 stimulation which was comparable to the mouse DP receptor response. The EC50 values were 0.8 nM and 0.5 nM for the guinea pig and mouse DP cell lines, respectively and the maximal response was comparable with both receptors. In contrast, the parental HEK293-Gα16 cell line did not show an increase in intracellular cAMP in response to PGD2 stimulation.

REFERENCES

Arimura A, Yasui K, Kishino J, Asanuma F, Hasegawa H, Kakudo S, Ohtani M, Arita H (2001). Prevention of allergic inflammation by a novel prostaglandin receptor antagonist, S-5751. J Pharmacol Exp Ther. 298(2), 411-9

Armstrong, R. A. 1996 Platelet prostanoid receptors. Pharmacol. Ther. 72:171-191.

Boie, Y., Sawyer, N., Slipetz, D. M., Metters, K. M., Abramovitz, M. 1995 Molecular cloning and characterization of the human prostanoid DP receptor. J. Biol. Chem. 270:18910-18916.

Brightling C E, Bradding P, Pavord I D, Wardlaw A J (2003). New Insights into the role of the mast cell in asthma. Clin Exp Allergy 33, 550-556

Coleman, R. A., Smith, W. L., Narumiya, S. 1994 VIII. International union of pharmacology classification of prostanoid receptors: properties, distribution, and structure of the receptors and their subtypes. Pharmacol. Rev. 46:205-229.

Doyle W J, Boehm S, Skoner D P (1990) Physiologic responses to intranasal dose-response challenges with histamine, methacholine, bradykinin, and prostaglandin in adult volunteers with and without nasal allergy. J Allergy Clin Immunol. 86(6 Pt 1), 924-35

Hirata, M., Kakizuka, A., Aizawa, M., Ushikubi, F., Narumiya, S. 1994 Molecular characterization of a mouse prostaglandin D receptor and functional expression of the cloned gene. 91:11192-11196.

Holgate S, Lackie P, Wilson S, Roche W, Davies D. (2000) Bronchial Epithelium as a key Regulator of Airway Allergen Sensisitzation and Remodelling in Asthma. Am J Respir Crit Care Med. 162, 113-117

Ito, S., Narumiya, S, and Hayaishi, O. 1989 Prostaglandin D2: a biochemical perspective Pros. Leuko. Essent. Fatty Acids 37:219-234.

Lewis, R A, Soter N A, Diamond P T, Austen K F, Oates J A, Roberts L J II (1982). Prostaglandin D2 generation after activation of rat and human mast cells with anti-IgE. J. Immunol 129, 1627-1631.

Matsuoka, T., Hirata, M., Tanaka, H., Takahashi, Y., Murata, T., Kabashima, K, Sugimoto, Y., Kobayashi, T., Ushikubi, F., Aze, Y., Eguchi, N., Urade, Y., Yoshida, N., Kimura, K, Mizoguchi, A., Honda, Y., Nagai, H., Narumiya, S. 2000 Prostaglandin D2 as a mediator of allergic asthma. Science 287:2013-2017.

Sambrook, et al., eds. Molecular Cloning: A Laboratory Manual, $2^{nd}$ ed., Cold Spring Harbor Press, Cold Spring Harbor, N.Y., 1989.

Roberts, L. J. II, Sweetman, B. J., Lewis, R. A., Austin, K. F., Oates, J. A. 1980 Increased production of prostaglandin D2 in patients with systemic mastocytosis. N. Eng. J. Med. 303:1400-1404.

Wright, D. H., Nantel, F., Metters, K. M., Ford-Hutchinson, A. W. 1999 A novel biological role for prostaglandin $D_2$ is suggested by distribution studies of the rat DP prostanoid receptor. Eur. J. Pharmacol. 377:101-115.

What is claimed is:

1. A recombinant polypeptide comprising the amino acid sequence of SEQ ID NO:2.

2. The recombinant polypeptide of claim 1 further comprising a detectable label.

3. The recombinant polypeptide of claim 2, wherein the detectable label comprises an enzyme, a radio active isotope, or a chemical which fluoresces.

4. A recombinant polypeptide comprising an amino acid sequence at least 95% identical to the sequence of SEQ ID NO:2 and which binds a prostanoid.

5. A recombinant polypeptide comprising an amino acid sequence at least 99% identical to the sequence of SEQ ID NO:2 and which binds a prostanoid.

* * * * *